US005834504A

United States Patent [19]
Tang et al.

[11] Patent Number: 5,834,504
[45] Date of Patent: Nov. 10, 1998

[54] 3-(2'-HALOBENZYLIDENYL)-2-INDOLINONE COMPOUNDS FOR THE TREATMENT OF DISEASE

[75] Inventors: Peng Cho Tang, Moraga; Li Sun, Foster City; Gerald McMahon, Kenwood, all of Calif.

[73] Assignee: Sugen, Inc., Redwood City, Calif.

[21] Appl. No.: 655,225

[22] Filed: Jun. 5, 1996

Related U.S. Application Data

[63] Continuation-in-part of Ser. No. 485,323, Jun. 7, 1995.
[51] Int. Cl.⁶ .................... H61K 31/40; C07D 209/34
[52] U.S. Cl. .................................. 514/418; 548/486
[58] Field of Search ............................ 548/486; 514/418

[56] References Cited

U.S. PATENT DOCUMENTS

| | | | |
|---|---|---|---|
| 2,872,372 | 2/1959 | Hull | 514/418 |
| 2,968,557 | 1/1961 | Burgardt et al. | 514/469 |
| 4,642,309 | 2/1987 | Michel et al. | 514/469 |
| 4,827,847 | 5/1989 | Michel et al. | 514/256 |
| 4,853,403 | 8/1989 | Shiraishi et al. | 514/404 |
| 4,868,304 | 9/1989 | Larock et al. | 546/141 |
| 4,966,849 | 10/1990 | Vallee et al. | 435/199 |
| 4,971,996 | 11/1990 | Shiraishi et al. | 514/521 |
| 5,051,417 | 9/1991 | Nadler et al. | 514/222.5 |
| 5,057,538 | 10/1991 | Shiraishi et al. | 514/521 |
| 5,089,516 | 2/1992 | Shiraishi et al. | 514/404 |
| 5,124,347 | 6/1992 | Conner et al. | 514/418 |
| 5,202,341 | 4/1993 | Shiraishi et al. | 514/469 |
| 5,206,261 | 4/1993 | Kawaguchi et al. | 514/418 |
| 5,217,999 | 6/1993 | Levitzki et al. | 514/613 |
| 5,302,606 | 4/1994 | Spada et al. | 514/357 |
| 5,322,950 | 6/1994 | Sircar et al. | 548/753 |
| 5,330,992 | 7/1994 | Eissenstat et al. | 514/312 |
| 5,374,652 | 12/1994 | Buzzetti et al. | 514/418 |
| 5,382,593 | 1/1995 | Le Baut et al. | 514/418 |
| 5,397,787 | 3/1995 | Buzzetti et al. | 514/300 |
| 5,409,949 | 4/1995 | Buzzetti et al. | 514/414 |
| 5,463,052 | 10/1995 | Haga et al. | 544/2 |

FOREIGN PATENT DOCUMENTS

| | | |
|---|---|---|
| 286870 | 11/1967 | Australia . |
| 2012634 | 9/1991 | Canada . |
| 351213 | 1/1990 | European Pat. Off. . |
| 525472 | 2/1993 | European Pat. Off. . |
| 566 266 | 10/1993 | European Pat. Off. . |
| 580502 | 1/1994 | European Pat. Off. . |
| 0626377 | 11/1994 | European Pat. Off. . |
| 632102 | 1/1995 | European Pat. Off. . |
| 0 632 102 | 4/1995 | European Pat. Off. . |
| 662473 | 7/1995 | European Pat. Off. . |
| 0788890 | 8/1997 | European Pat. Off. . |
| 1.3988.224 | 3/1965 | France . |
| 1398224 | 5/1965 | France . |
| 2689397 | 8/1993 | France . |
| 878539 | 6/1953 | Germany . |
| 2159360 | 4/1973 | Germany . |
| 2159361 | 4/1973 | Germany . |
| 2159362 | 4/1973 | Germany . |
| 2159363 | 4/1973 | Germany . |
| 2321656 | 11/1973 | Germany . |
| 3310891 | 9/1984 | Germany . |
| 3426419 | 1/1986 | Germany . |
| 62-29570 | 2/1987 | Japan . |
| 62-39564 | 2/1987 | Japan . |
| 63-141955 | 6/1988 | Japan . |
| 5-58894 | 3/1993 | Japan . |
| 9286777 | 11/1997 | Japan . |
| 809691 | 3/1959 | United Kingdom . |
| 835473 | 5/1960 | United Kingdom . |
| 1384599 | 2/1975 | United Kingdom . |
| WO 88/07035 | 9/1988 | WIPO . |
| WO 91/13055 | 5/1991 | WIPO . |
| WO 91/15495 | 10/1991 | WIPO . |
| WO 92/07830 | 5/1992 | WIPO . |
| WO 92/20642 | 11/1992 | WIPO . |
| Wo 92/21660 | 12/1992 | WIPO . |
| WO 93/01182 | 1/1993 | WIPO . |
| WO 94/03427 | 2/1994 | WIPO . |
| WO 94/10202 | 5/1994 | WIPO . |
| WO 94/14808 | 7/1994 | WIPO . |
| WO 95/01349 | 1/1995 | WIPO . |
| 9514667 | 6/1995 | WIPO . |
| WO 95/17181 | 6/1995 | WIPO . |
| WO 96/00226 | 1/1996 | WIPO . |
| WO 96/16964 | 6/1996 | WIPO . |
| WO 96/22976 | 8/1996 | WIPO . |
| WO 96/32380 | 10/1996 | WIPO . |
| WO 96/40116 | 12/1996 | WIPO . |
| 9725986 | 7/1997 | WIPO . |
| 9736867 | 10/1997 | WIPO . |

OTHER PUBLICATIONS

Howard, Provisional Patent Application No. 60/015,134 filed Mar. 29, 1996 for "Lactam Derivatives".

Andreani et al., "Potential Antitumor Agents. 25[1]. Synthesis and Cytotoxic Activity of 3–(2–Chloro–3–Indolylmethlene) 1,3–Dihydroindol–2–Ones," *AntiCancer Research* 16:3585–3588 (1996).

Terrett et al., "Combinatorial Synthesis—The Design of Compound Libraries and their Application to Drug Discovery," *Tetrahedron* 51(30):8135–8173 (1995).

Coda et al., "3–(4–methylbenzilidene)–1–, 3–dihydroindol–2–one," *Journal of the Chemical Society, Perkin Transactions* 2 4:615–620 (1984), Database Crossfire, Beilstein No. 6–21.

Wahl, "3–benzilidene–5–methyl–1,3–dihydroindol–2–one," *Ann. Chim* p. 350 (1926), Database Crossfire, Beilstein No. 2–21–00–00290.

Elliot, "1–methyl–2–(3–oxindolidenmethyl)–pyridinium," *Journal of Organic Chemistry* 29:2438–2440 (1964), Database Crossfire, Beilstein No.5–24.

(List continued on next page.)

*Primary Examiner*—Richard L. Raymond
*Attorney, Agent, or Firm*—Lyon & Lyon LLP

[57] ABSTRACT

The present invention relates to organic molecules capable of modulating tyrosine kinase signal transduction in order to regulate, modulate and/or inhibit abnormal cell proliferation.

24 Claims, No Drawings

OTHER PUBLICATIONS

Akbasak, A., and Sunar–Akbasak, B. (1992). Oncogenes: cause or consequence in the development of glial tumors. Journal of the Neurological Sciences 111, 119–133.

Arteaga, C. L., Kitten, L. J., Coronado, E. B., Jacobs, S., Kull, F. C. J., Allred, D. C., and Osborne, C. K. (1989). Blockade of the type I somatomedin receptor inhibits growth of human breast cancer cells in athymic mice. J. Clin. Invest. 84, 1418–1423.

Baserga, R. (Dec. 1994). Oncogenes and the strategy of growth factors. Cell 79, 927–930.

Baserga, R. (Jan. 1995). The insulin–like growth factor I receptor: a key to tumor growth? Cancer Research 55, 249–252.

Bolen, J. B., Rowley, R. B., Spana, C., and Tsygankov, A. Y. (1992). The Src family of tyrosine protein kinases in hemopoietic signal transduction. FASEB Journal 6, 3403–3409.

Bolen, J.B. (1993). Nonreceptor tyrosine protein kinases. Oncogene 8, 2025–2031.

Coppola, D., et al. (Jul. 1994). A functional insulin–like growth factor I receptor is required for the mitogenic and transforming activities of the epidermal growth factor receptor. Molecular and Cellular Biology 14, 4588–4595.

Dati, C., Antoniotti, S., Taverna, D., Perroteau, I,. and De Bortoli, M. (1990). Inhibition of c–erB–2 oncogene expression by estrogens in human breast cancer cells. Oncogene 5, 1001–1006.

Decker, T., and Lohmann–Matthes, M.–L. (1988). A quick and simple method for quantitation of lactate dehydrogenase release in measurements of cellular cytotoxicity and tumor necrosis factor (TNF) activity. J. of Imm. Methods 15, 61–69.

Dickson, R. B., Salomon, D. S., and Lippman, M. E. (1991). Tyrosine kinase receptor—nuclear protooncogene interactions in breast cancer. Cancer Treatment and Research 61, 249–273.

Fantl, W. J., et al. (1992). Distinct Phosphotyrosines on a growth factor receptor bind to specific molecules that mediate different signaling pathways. Cell 69, 413–423.

Fendly, B. M. (1990). Characterization of murine monoclonal antibodies reactive to either the human epidermal growth factor receptor of or HER2/neu gene product. Cancer Research 50, 1550–1558.

Fingl, E., and Woodbury, D. M. (1975). The Pharmacological Basis of Therapeutics Chapter I, 1–46.

Floege, J., Eng, E., Young, B. A., and Johnson, R. J. (1993). Factors involved in the regulation of mesangial cell proliferation in vitro and in vivo. Kidney International 43, S–47 –S–54.

Goldring, M. B., and Goldring, S. R. (1991). Cytokines and cell growth control. Critical Reviews in Eukaryotic Gene Expression 1, 301–326.

Gottardis, M. M., Robinson, S. P., and Jordan, C. V. (1988). Estradiol–stimulated growth of MCF–7 tumors implanted in athymic mice: A model to study the tumoristatic action of tamoxifen. J. Steroid Biochem. 30, 311–314.

Honegger, A. M., et al. (1987). Point mutation at the ATP binding site of EGF receptor abolishes protein–tyrosine kinase activity and alters cellular routing. Cell 51, 199–209.

Jellinek, D., Green, L. S., and Janjic, N. (Aug. 1994). Inhibition of receptor binding by high–affinity RNA ligands to vascular endothelial growth factor. Biochemistry 33, 10450–10456.

Kendall, R. L., and Thomas, K. A. (1993). Inhibition of vascular endothelial cell growth factor activity by an endogenously encoded soluble receptor. Proc.Natl.Acad.Sci. 90, 10705–10709.

Kim, K. J., Li, B., Winer, J., Armanini, M., Gillett, N., Phillips, H. S., and Ferrara, N. (1993). Inhibition of vascular endothelial growth factor–induced angiogenesis suppresses tumour growth in vivo. Nature 362, 841–844.

Kinsella, J. L., Grant, D. S., Weeks, B. S., and Kleinman, H. K. (1992). Protein kinase C regulates endothelial cell tube formation on basement membrane matrix, matrigel. Experimental Cell Research 199, 56–62.

Koch, C. A., Anderson, D., Moran, M. F., Ellis, C., and Pawson, T. (1991): SH2 and SH3 domains: elements that control interactions of cytoplasmic signaling proteins. Science 252, 668–674.

Korc, M., et al. (1992). Overexpression of the epidermal growth factor receptor in human pancreatic cancer is associated with concomitant increases in the levels of epidermal growth factor and transforming growth factor alpha. J. Clin. Inv. 90, 1352–60.

Korzseniewski, C., and Callewaert, D. M. (1983). An enzyme–release assay for natural cytotoxicity. Journal of Immunological Methods 64, 313–320.

Kumabe, T., et al. (1992). Amplification of alpha–platelet–derived growth factor receptor gene lacking an exon coding for a portion of the extracellular region in a primary brain tumor of glial origin. Oncogene 7, 627–633.

Lee, B. A., and Donoghue, D. J. (1992). Intracellular retention of membrane–anchored v–sis protein abrogates autocrine signal transduction. The Journal of Cell Biology 118, 1057–1070.

Macaulay, V. M., Everard, M. J., Teale, J. D., Trott, P. A., Van Wyk, J. J., and Smith, I. E. (1990). Autocrine function for insulin–like growth factor I in human small cell lung cancer cell lines and fresh tumor cells. Cancer Research 50, 2511–2517.

Mariani, M., et al. (Mar. 1994). Inhibition of angiogenesis by PCE26806, a potent tyrosine kinase inhibitor. Proceedings of the American Association for Cancer Research 35, 381.

Mosmann, T. (1983). Rapid Colorimetric assay for cellular growth and survival: application to proliferation and cytotoxicity assays. Journal of Immunological Methods 65, 55–63.

Osborne, C. K., Hobbs, K., and Clark, G. M. (1985). Effect of estrogens and antiestrogens on growth of human breast cancer cells in athymic nude mice. Cancer Research 45, 584–590.

Ozzello, L., and Sordat, M. (1980). Behavior of tumors produced by transplantation of human mammary cell lines in athymic nude mice. Europ. J. Cancer 16, 553–559.

Plowman, G. D. et al. (Aug. 1994). Receptor tyrosine kinases as targets for drug intervention. DN&P 7, 334–339.

Rygaard, J., and Poulson, C. O. (1969). Heterotransplantation of a human malignant tumour to "nude" mice. Acta. path. microbiol scand. 77, 758–760.

Sandberg–Nordqvist, A.–C., Stahlbom, P.–A., Reinecke, M., Collins, P. V., von Holst, H., and Sara, V. (1993). Characterization of insulin–like growth factor 1 in human primary brain tumors. Cancer Research 53, 2475–2478.

Schlessinger, J., and Ullrich, A. (1992). Growth factor signaling by receptor tyrosine kinases, Neuron, 9, 383–391.

Seibert, K., Shafie, S. M., Triche, T. J., Whang–Peng, J. J., O'Brien, S. J., Toney, J. H., Huff, K. K., and Lippman, M. E. (1983). Clonal variation of MCF–7 breast cancer cells in vitro and in athymic nude mice. Cancer Research 43, 2223–2239.

Shafie, S. M., and Grantham, F. H. (1981). Role of hormones in the growth and regression of human breast cancer cells (MCF–7) transplanted into athymic nude mice. JNCI 67, 51–56.

Skehan, P., et al. (1990). New Colorimetric cytotoxicity assay for anticancer–drug screening. Journal of the National Cancer Institute 82, 1107–1112.

Slamon, D. J., et al. (1989). Studies of the HER–2/neu Proto–oncogene in Human Breast and Ovarian Cancer. Science 244, 707–712.

Songyang, Z., et al. (1993). SH2 domains recognize specific phosphopeptide sequences. Cell 72, 767–778.

Songyang, Z., et al. (Apr. 1994). Specific motifs recognized by the SH2 domains of Csk, 3PB2, fps/fes, GRB–2, HCP, SHC, Syk, and Vav. Molecular and Cellular Biology 14, 2777–2785.

Takano, S., Gately, S., Jiang, J. B., and Brem, S. (1993). Inhibition of angiogenesis by a novel diaminoanthraquinone that inhibits protein kinase C. Mol. Bio. of the Cell 4, 358A.

Torp, S. H., Helseth, E., Ryan, L., Stolan, S., Dalen, A., and Unsgaard, G. (1992). Expression of the epidermal growth factor receptor gene in human brain metastases. APMIS 100, 713–719.

Tuzi, N. L., Venter, D. J., Kumar, S., Staddon, S. L., Lemoine, N. R., and Gullick, W. J. (1990). Expression of growth factor receptors in human brain tumours. British J. of Cancer 63, 227–233.

Ullrich, A., and Schlessinger, J. (1990). Signal transduction by receptors with tyrosine kinase activity. Cell 62, 203–212.

Voller, A., Bidwell, D., and Barlett, A. Enzyme–linked immunosorbent assay. Manual of Clinical Immunology, 2nd ed., 359–371 (1972).

Wärri, A. M., et al. (1991). Estrogen suppresson of erbB2 expression is associated with increased growth rate of ZR–75–1 human breast cancer cells in vitro and in nude mice. Int. J. Cancer 49, 616–623.

Wright, P.S., Cross–Doersen, D., Miller, J. A., Jones, W. D., and Bitonti, A. J. (1992). Inhibition of angiogenesis in vitro and in ovo with an inhibitor of cellular protein kinases, MDL 27032. Journal of Cellular Physiology 152, 448–457.

Andreani, A., M. Rambaldi, A. Locatelli, R. Bossa, and I. Galatulas. 1990. Synthesis and cardiotonic activity of 2–indolinones. Eur. J. Med. Chem. 25:187–190.

Blake, K. W., and B. Jaques. 1973. Anisotropic Effects in alpha–substituted methoxystilbenes. J.C.S. Perkin II :1660–1663.

Canoira, L., and J. G.Rodriguez. 1985. Synthesis of Oxindole Derivatives from N–Alkenyl–o–Chloroanilides with Zero–Valent Nickel Complex. J. Heterocyclic Chem. 22:1511–1518.

Chatten, L. G., R. W. Daisley, and C. J. Olliff. 1973. Substituted Oxindoles. Part VI. Polargraphic Reduction of Substituted trans–3–benzylideneindol–2(3H)–ones. J.C.S. Perkin II :469–473.

Coda, A., Corsico, A. G. Invernizzi, P. P. Righetti, and G. Tacconi. 1984. (Z)–and (E)–Arylidene–1, 3–dihydroindol–2–ones: Configuration, Conformation, and Infrared Carbonyl Stretching Frequencies. J. Chem. Soc.Perkin Trans. II:615–619.

Daisley, R. W. 1974. Thin–layer chromatographic separation of some substituted 3–benzylidene–indol–2(3H)–ones. Journal of Chromatography 100:240–242.

Hewgill, F. R., and J. M. Stewart. 1988. Phenanthrene–4, 5–quinones: a Synthesis of Morphenol. J. Chem. Soc.Perkin Trans. 1:1305–1311.

Hodges, R., J. F. Shannon, W. D. Jamieson, and A. Taylor. 1968. Chemical and biological properties of some oxindolidyl–3–methines. Canadian Journal of Chemistry 46:2189–2194.

Ijaz, A. S., J. Parrick, and A. Yahya. 1990. The Conversion of o, beta–Dinitrostyrenes into Indoles and the Preparation of Oxindole Quinones. J. Chem Research (S):116.

Katritzky, A.R., Q.–L. Li, and W.–Q. Fan. 1988. Color and Constitution. Part 8. Some novel dyestuffs containing indoxyl residues. J. Heterocyclic 25:1287–1292.

Khalil, Z., H., and A. E. Abdel–Rahman. 1977. Synthesis of New Mero–and Asymmetrical Pyrazolo–Monomethine Cyanine Dyes. J. Indian Chem. Soc. LIV:904–907.

Kobayashi, G., Y. Matsuda, Y. Tominaga, M. Ohkuma, H. Shinoda, M. Kohno, and D. i. Mizuno. 1977. Anti–tumor activity of indole derivatives. Yakugaku Zasshi 97:1033–39.

Kovac, J., and J. Stetinova. 1976. Furan derivatives LXXX. Synthesis and properties of substituted furfurylidenoxindoles. Chem. rvesu 30:484–492.

Larock, R. C., and S. Babu. 1987. Synthesis of Nitrogen Heterocycles via Palladium–catalyzed Intramolecular Cyclization.Tetrahedron Letters 28:5291–5294.

Martin–Leon, N., M. Quinteiro, C. Seoane, and J. L. Soto. 1990. On the Cyclization to the Elusive Amino–4H–pyran Ring Some New Facts. Liebigs Ann. Chem. :101–104.

Mirand, C., G. Massiot, and J. Levy. 1982. A Synthetic Entry in the Aristotelia Alkaloids. J. Org. Chem. 47:4169–4170.

Nodiff, E. A., K. Tanabe, C. Seyfried, S. Matsuura, Y. Kondo, E. H. Chen, and M. P. Tyagi. 1971. Antimalarial Phenanthrene Amino Alcohols. 1. Fluorine–Containing 3–and 6–Substituted 9–Phenanthrenemethanols. Journal of Medicinal Chemistry 14:921–925.

Ruveda, E. A., and H.A. Gonzalez. 1970. Geometric isomerism in benzylideneoxindoles. Spectrochimica Acta 26A:1275–1277.

Schnierle, v. F., H. Reinhard, N. Dieter, E. Lippacher, and H. von Dobenick. 1968. Vilsmeier–Reaktion mit Pyrrol–und Pyrrolon–Derivaten. Liebigs. Ann Chem. 715:90–97.

Stetinova, J., J. Kovak, J. Sura, and M. Dandarova. 1977. Stereochemistry and photoisomeirsation of furfurylideneoxindoles. Collection Czechoslov. Chem. Commun. 42:2201–06.

Tacconi, G., L. D. Maggi, P. Righetti, G. Desimoni, O. Azzolina, and V. Ghislandi. 1976. (Z)–and (E)–3–Alkylidene–1,3–dihydroindol–2–ones: Influence of Configuration on the Transmission of the Inductive Effect to the Carbonyl Group. JCS Perkin II :150–15.

Thompson, A. M., M. Boyd, and W. A. Denny. 1993. Facile Dimerisation of 3–Benzylideneindoline–2–thiones. J. Chem. Soc. Perkin Trans. 1:1835–1837.

Triebs, v. A., K. Jacob, and A. Dietl. 1967. Über isoindigoide Farbstroffe der Pyrrol–Reihe. Liebigs Ann. Chem. 702:122–130.

Varma, R. S., and P. Gupta. 1989. Nucleophilic Reactions of 2–Methyl–3–(4'–carbomethoxy–phenyl)–4–quinazolines with 2–indolinones. J. Indian Chem. Soc. 66:804–805.

von Dobeneck, H., D. Wokenstein, and G. Blankenstein. 1968. a.b–Diindolylmethane und–methene. Der Urorosein–Chromophor. Zur Chemie des Indols VI:1347–1357.

Bahner, C.T., Brotherton, D. H., and Kinder, H. 1969. Benzylideneindenes with Oxygen Attached to the Indene Ring. J. Med. Chem. 12:721–2.

Bahner, C.T., Brotherton, D.H., Kinder, H., Rich, W., Watson, S.L. Jr., and Zirkle, J. 1969. Benzylideneindenes with Oxygen Attached to the Indene Ring. J. Med. Chem. 12:722.

Abramovitch, R. A., and Hey, D. H. (1954). Internuclear cyclisation. J. Chem. Soc., 1697–1703.

Abramovitch, R. A., Coutts, R. T., and Pound, N. J. (1967). A novel synthesis of a cyclic hydroxamic acid involving a molecular rearrangement. Chemistry and Industry 44, 1871.

Andreani, A., Rambaldi, M., Locatelli, A., Bongini, A., Bossa, R., Galatulas, I., and Ninci, M. (1992). Synthesis and cardiotonic activity of pyridylmethylene–2–indolinones. J. Med Chem 27, 167–170.

Andreani, A., Rambaldi, M., Locatelli, A., Leoni, A., Bossa, R., Chiericozzi, M., Galatulas, I., and Salvatore, G. (1993). Synthesis of lactams with potential cardiotonic activity. J. Med. Chem 28, 825–829.

Andreani, A., Rambaldi, M., Leoni, A., Locatelli, A., Bossa, R., Chiericozzi, M., Dambrosio, M., and Galatulas, I. (1993). Synthesis and cardiotonic activity of 2–indolinones bearing pyridyl groups. J. Med Chem. 28, 653–647.

Autrey, R. L., and Tahk, F. C. (1967). The synthesis and sterochemistry of some isatylideneacetic acid derivatives. Tetrahedron 23, 901–917.

Bamfield, P., Johnson, A. W., and Katner, A. S. (1966). Diels–Alder reactions of oxindolylideneacetone. J. Chem. Soc. (C) C, 1028–1030.

Borsche, W., Wagner–Roemmich, M., and Barthenheier, J. (1941). Über nielkernige kondersierte systeme mit heterocyclischen ringen. Liebigs Ann. Chem. 550, 160–174.

Buzzett, F., Brasca, M. G., Crungola, A., Fustinoni, S., Longo, A., and Penco, S. (1993). Cinnamamide analogs as inhibitors of protein tyrosine kinases. Il Farmaco 48, 615–636.

Elliott, I. W., and Rivers, P. (1964). Reduction of some oxindolylidene derivatives to 3–substituted oxindoles by sodium borohydride. J. Org. Chem. 29, 2438–40.

Howard, H., Sarges, R., Siegel, T., and Beyer, T. (1992). Synthesis and aldose reductase inhibitory activity of substituted 2(1H)–benzimidazolone–and oxindole–1–acetic acids. Eur J Med Chem 27, 779–789.

Neber, P. W., and Röcker, E. (1923). Ueber die einwirkung von benzaldehyden auf die freie o–aminophenyl–essigsäure. Chem. Ber. 56, 1710–1717.

O'Sullivan, W. I., and Rothery, E. J. (1975). The preparation and possible clinical significance of 4'–dialkylaminoisoindogenides. Clinica Chimica Acta 62, 181–182.

Pavlenko, N. I., Marshtupa, V. P., and Baranov, S. N. (1980). Introduction of aminomethyl groups into heterocyclic CH–acid molecules. Dopov. Akad. Nauk Ukr, RSR 7, 64–66.

Schindler, v. O., Blaser, R., and Hunziker, F. (1966). Über dibenz[b,f]–azocin–derivate. Helvetica Chimica Acta 49, 985–9.

Shiraishi, T., Domoto, T., Imai, N., Shimada, Y., and Watanabe, K. (1987). Specific inhibitors of tyrosine–specific protein kinase, synthetic 4–hydroxycinnamamide derivatives. Biomedical and Biophysical Research Communications 147, 322–328.

Shiraishi, T., Owada, M. K., Tatsuka, M., Yamashita, T., Watanabe, K., and Kakunaga, T. (1989). Specific inhibitors of tyrosine–specific protein kinases: properties of 4–hydroxycinnamamide derivates in vitro. Cancer Research 49, 2374–78.

Sumpter, W. C., and Miller, F. M. (1954). Heterocyclic compounds with indole and carbazole systems. Interscience Publishers Inc. Ch. IV Oxindole, 134–153.

Tacconi, G., and Marinone, F. (1968). Preparazione e caratteristiche di alcuni 3–ossindolidenderivati. Ricerca Scientifica 38, 1239–1244.

Wahl, A., Bagard, P., and Haller, M. A. (1909). Chimie Organique—Sur les iso–indogénides. C.R. Hebd. Seances Acad. Sci. 149, 132–134.

Walker, G. N. (1965). Synthesis of a–(p–aminophenyl)–and a–(p–chlorophenyl)–b–aryl–propiontriles by catalytic reduction of stilbenenitriles. J Med Chem 8(5), 583–588.

Walker, G. N. et al. (1965). Synthesis of New 3–(Pyridylmethylene)–, 3–(Pyridylmethyl)–, 3–Piperidylmethyl)–, and 3–(β–Alkylaminoethyl)–2–indolinones. J. Med Chem 8(5), 626–37.

Winkelman, E., Raether, W., Gebert, U., and Sinharay, A. (1977). Chemotherapeutically active nitro compounds. Arzneim.–Forsch/Drug Res. 27, 2251–2263.

Wright, W. B., and Collins, K. H. (1956). Cyclic hydroxamic acids derived from indole. JACS 78, 221–224.

Young, T. E., and Babbitt, B. W. (1982). 2–(2–methyl–3–indolyl)–1,4–benzoquinone, a reversible redox substrate at the carbon–paste electrode in acidic aqueous–ethanolic media. J. Org. Chem 47, 1571–1572.

Zhungietu, G. I., Dragalina, G. A., and Dorofeenko, G. N. (1975). Reaction of indoles and 2–ketoindolines with some aldehydes. Khimiya Geterotsiklicheskikh Soedinenii 1, 40–44.

Beilstein Reg. No.: 252929 Beilstein (1923).

3-(2'-HALOBENZYLIDENYL)-2-INDOLINONE COMPOUNDS FOR THE TREATMENT OF DISEASE

This application is a continuation-in-part of U.S. patent application Ser. No. 08/485,323, filed Jun. 7, 1995, which is hereby incorporated by reference in its entirety.

1. INTRODUCTION

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell proliferative and metabolic disorders.

2. BACKGROUND OF THE INVENTION

Protein tyrosine kinases (PTKs) comprise a large and diverse class of proteins having enzymatic activity. The PTKs play an important role in the control of cell growth and differentiation (for review, see Schlessinger & Ullrich, 1992, *Neuron* 9:383–391).

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signalling molecules that facilitate the appropriate cellular response (e.g., cell division, metabolic effects to the extracellular microenvironment). See, Schlessinger and Ullrich, 1992, *Neuron* 9:383–391.

With respect to receptor tyrosine kinases, it has been shown also that tyrosine phosphorylation sites function as high-affinity binding sites for SH2 (src homology) domains of signaling molecules. Fantl et al., 1992, *Cell* 69:413–423; Songyang et al., 1994, *Mol. Cell. Biol.* 14:2777–2785); Songyang et al., 1993, *Cell* 72:767–778; and Koch et al., 1991, *Science* 252:668–678. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. Songyang et al., 1993, *Cell* 72:767–778. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

Receptor Tyrosine Kinases. The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses. Ullrich & Schlessinger, 1990, *Cell* 61:203–212.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al., 1994, *DN&P* 7 (6):334–339, which is incorporated herein by reference.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, *Oncogene* 8:2025–2031, which is incorporated herein by reference.

Many of the tyrosine kinases, whether an RTK or non-receptor tyrosine kinase, have been found to be involved in cellular signaling pathways leading to cellular signal assays signalling pathways leading to pathogenic conditions, including cancer, psoriasis and hyper immune response.

Development Of Compounds To Modulate The PTKs. In view of the surmised importance of PTKs to the control, regulation and modulation of cell proliferation and the diseases and disorders associated with abnormal cell proliferation, many attempts have been made to identify receptor and non-receptor tyrosine kinase "inhibitors" using a variety of approaches, including the use of mutant ligands (U.S. patent application Ser. No. 4,966,849), soluble receptors and antibodies (Application Ser. No. WO 94/10202; Kendall & Thomas, 1994, *Proc. Nat'l Acad. Sci* 90:10705–09; Kim, et al., 1993, *Nature* 362:841–844), RNA ligands (Jellinek, et al., *Biochemistry* 33:10450–56); Takano, et al., 1993, *Mol. Bio. Cell* 4:358A; Kinsella, et al., 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642), vinylene-azaindole derivatives (PCT WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and the object of this invention.

3. SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, arthritis and restenosis and metabolic diseases such as diabetes.

In one illustrative embodiment, the compounds of the present invention have the formula:

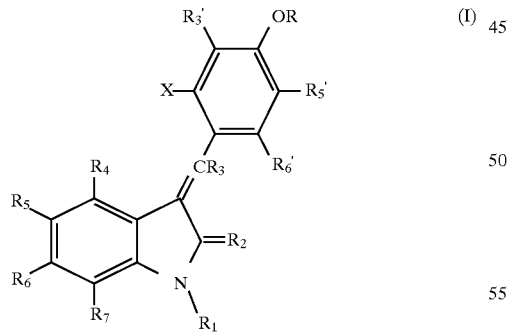

and pharmaceutically acceptable salts thereof, wherein $R_1$ is H or alkyl;

$R_2$ is O or S;

$R_3$ is hydrogen;

$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

$R_3'$, $R_5'$, and $R_6'$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

n is 0–3;

X is Br, Cl, F or I;

R is H, alkyl or aryl; and

R' is H, alkyl or aryl.

In another illustrative embodiment, the compounds of the present invention have the formula:

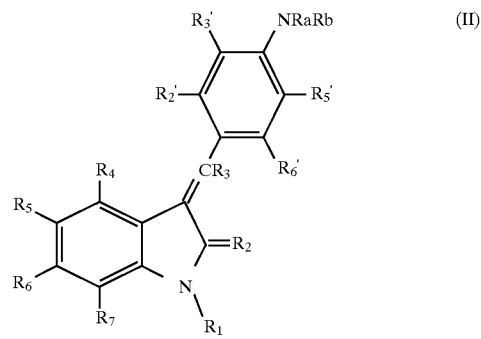

and pharmaceutically acceptable salts thereof, wherein $R_1$ is H or alkyl;

$R_2$ is O or S;

$R_3$ is hydrogen;

$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

$R_2'$, $R_3'$, $R_5'$, and $R_6'$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

Ra and Rb are each independently selected from the group consisting of H, alkyl and C(O)R, or NRaRb taken together may be a heterocyclic ring of from 3 to 8 atoms optionally substituted at one or more positions with hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

n is 0–3;

X is Br, Cl, F or I;

R is H, alkyl or aryl; and

R' is H, alkyl or aryl.

In yet another illustrative embodiment, the compounds of the present invention have the formula:

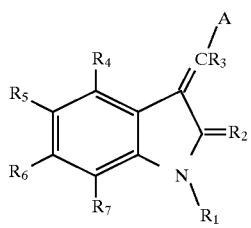

(III)

and pharmaceutically acceptable salts thereof, wherein
$R_1$ is H or alkyl;
$R_2$ is O or S;
$R_3$ is hydrogen;
$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';
A is a five membered heteroaryl ring selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, optionally substituted at one or more positions with alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ or CONRR';
n is 0–3;
X is Br, Cl, F or I;
R is H, alkyl or aryl; and
R' is H, alkyl or aryl.
In still another illustrative embodiment, the compounds of the present invention have the formula:

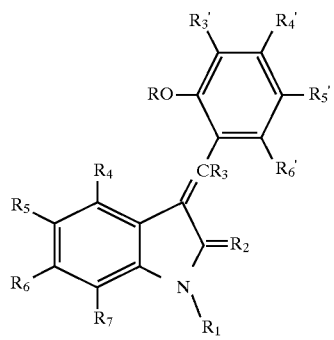

(IV)

and pharmaceutically acceptable salts thereof, wherein:
$R_1$ is H or alkyl;
$R_2$ is O or S;
$R_3$ is hydrogen;
$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';
$R_{3'}$, $R_{4'}$, $R_{5'}$, and $R_{6'}$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';
n is 0–3;
X is Br, Cl, F or I;
R is H, alkyl or aryl; and
R' is H, alkyl or aryl.
In a final illustrative embodiment, the compounds of the present invention have the formula:

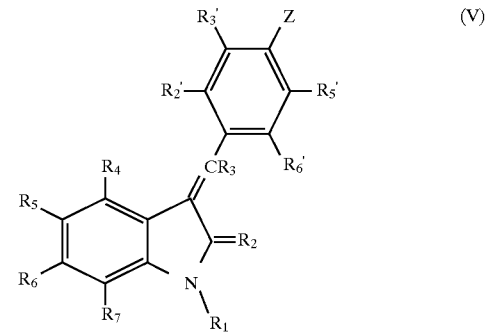

(V)

and pharmaceutically acceptable salts thereof, wherein:
$R_1$ is H or alkyl;
$R_2$ is O or S;
$R_3$ is hydrogen;
$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR';
$R_{2'}$, $R_{3'}$, $R_{5'}$, and $R_{6'}$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR';
n is 0–3;
Z is Br, Cl, F, I, methyl, ethyl, n-propyl, iso-propyl, n-butyl, iso-butyl or tert-butyl;
R is H, alkyl or aryl; and
R' is H, alkyl or aryl.

The present invention is further directed to pharmaceutical compositions comprising a pharmaceutically effective amount of the above-described compounds of formulae I–V and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

DETAILED DESCRIPTION OF THE INVENTION 4.1. Definitions

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, more preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, $N(CH_3)_2$ amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, more preferably 1 to 4 carbons. The alkenyl group may be optionally substituted with one or more substituents selected from the group consisting of hydroxyl, cyano, alkoxy, =O, =S, $NO_2$, halogen, $N(CH_3)_2$ amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, more preferably 1 to 4 carbons. The alkynyl group may be optionally substituted with one or more substituents selected from the group consisting of hydroxyl, cyano, alkoxy, =O, =S, $NO_2$, halogen, $N(CH_3)_2$ amino, and SH.

"Alkoxy" refers to an "-Oalkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Amide" refers to —C(O)—NH—R, where R is alkyl, aryl, alkylaryl or hydrogen.

"Thioamide" refers to —C(S)—NH—R, where R is alkyl, aryl, alkylaryl or hydrogen.

"Amine" refers to a —N(R')R" group, where R' and R" are independently selected from the group consisting of alkyl, aryl, and alkylaryl.

"Thioether" refers to —S—R, where R is alkyl, aryl, or alkylaryl.

"Sulfonyl" refers to —S(O)$_2$—R, where R is aryl, C(CN) =C—aryl, $CH_2CN$, alkyaryl, sulfonamide, NH-alkyl, NH-alkylaryl, or NH-aryl.

4.2. The Invention

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signalling molecules that facilitate the appropriate cellular response (e.g., cell division, metabolic effects to the extracellular micro environment). See, Schlessinger and Ullrich, 1992, *Neuron* 9:383–391.

It has been shown that tyrosine phosphorylation sites in growth factor receptors function as high-affinity binding sites for SH2 (src homology) domains of signaling molecules. Fantl et al., 1992, *Cell* 69:413–423; Songyang et al., 1994, *Mol. Cell. Biol.* 14:2777–2785); Songyang et al., 1993, *Cell* 72:767–778; and Koch et al., 1991, *Science* 252:668–678. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. Songyang et al., 1993, *Cell* 72:767–778. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. Songyang et al., 1993, *Cell* 72:767–778. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis).

This invention is therefore directed to compounds which regulate, modulate and/or inhibit tyrosine kinase signal transduction by affecting the enzymatic activity of the RTKs and/or the non-receptor tyrosine kinases and interfering with the signal transduced such proteins. More particularly, the present invention is directed to compounds which regulate, modulate and/or inhibit the RTK and/or non-receptor tyrosine kinase mediated signal transduction pathways as a therapeutic approach to cure leukemia and many kinds of solid tumors, including but not limited to carcinoma, sarcoma, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

4.3. The Compounds

In one embodiment, the invention provides compounds having the formula:

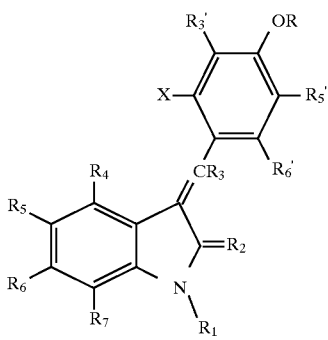

and the pharmaceutically acceptable salts thereof, wherein $R_1$ is H or alkyl;

$R_2$ is O or S;

$R_3$ is hydrogen;

$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

$R_{3'}$, $R_{5'}$, and $R_{6'}$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

n is 0–3;

X is Br, Cl, F or I; and

R is H, alkyl or aryl; and

R' is H, alkyl or aryl.

In a preferred embodiment of the compounds of formula I, $R_{3'}$ is selected from the group consisting of methyl, ethyl, n-propyl, iso-propyl, n-butyl, iso-butyl, tert-butyl, halogen, aryl and OR, where R is H, alkyl or aryl; and $R_{5'}$ is selected from the group consisting of hydrogen, methyl, ethyl, n-propyl, iso-propyl, n-butyl, iso-butyl, tert-butyl, halogen, aryl and OR, where R is H, alkyl or aryl.

A particularly preferred compound of formula I is 3-(2-chloro-4-hydroxybenzylidenyl)-2-indolinone (SU4932).

In another embodiment, the invention provides compounds having the formula:

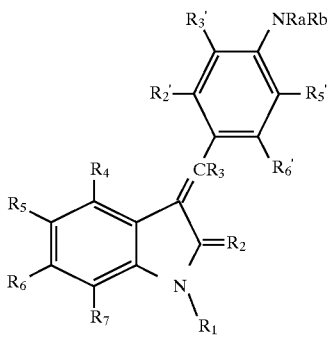

and the pharmaceutically acceptable salts thereof, wherein $R_1$ is H or alkyl;

$R_2$ is O or S;

$R_3$ is hydrogen;

$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

$R_{2'}$, $R_{3'}$, $R_{5'}$, and $R_{6'}$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

Ra and Rb are each independently selected from the group consisting of H, alkyl and C(O)R, or NRaRb taken together may be a heterocyclic ring of from 3 to 8 atoms optionally substituted at one or more positions with hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, or CONRR';

n is 0–3;

X is Br, Cl, F or I; and

R is H, alkyl or aryl; and

R' is H, alkyl or aryl.

In a preferred embodiment of the compounds of formula II, $R_{3'}$ is selected from the group consisting of methyl, ethyl, n-propyl, iso-propyl, n-butyl, iso-butyl, tert-butyl, halogen, aryl and OR, where R is H, alkyl or aryl; and $R_{5'}$ is selected from the group consisting of hydrogen, methyl, ethyl, n-propyl, iso-propyl, n-butyl, iso-butyl, tert-butyl, halogen, aryl and OR, where R is H, alkyl or aryl.

A particularly preferred compound of formula II is 3-(4-Dimethylaminobenzylidenyl)-2-indolinone (SU4312).

In yet another embodiment, the invention provides compounds having the formula:

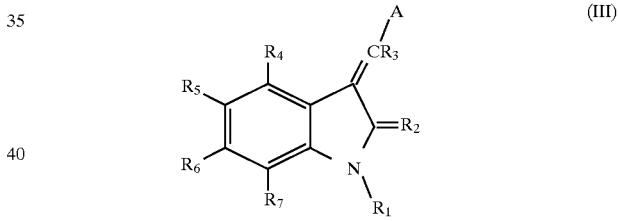

and the pharmaceutically acceptable salts thereof, wherein $R_1$ is H or alkyl;

$R_2$ is O or S;

$R_3$ is hydrogen;

$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

A is a five membered heteroaryl ring selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, optionally substituted at one or more positions with alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ or CONRR';

n is 0–3;

X is Br, Cl, F or I;

R is H, alkyl or aryl; and $R_1$ is H, alkyl or aryl.

In a preferred embodiment of the invention, the compound of formula III is 3-[(2,4-Dimethylpyrrol-5-yl)methylene]-2-indolinone (SU5416).

In still another embodiment, the invention provides compounds having the formula:

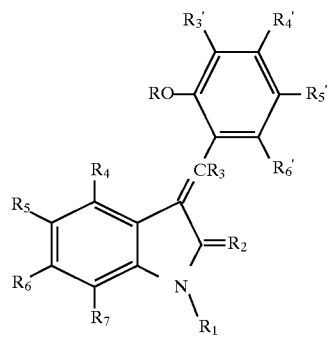

and the pharmaceutically acceptable salts thereof, wherein:

$R_1$ is H or alkyl;

$R_2$ is O or S;

$R_3$ is hydrogen;

$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR';

$R_{3'}$, $R_{4'}$, $R_{5'}$, and $R_{6'}$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

n is 0–3;

X is Br, Cl, F or I;

R is H, alkyl or aryl; and

R' is H, alkyl or aryl.

In a preferred embodiment of the compound of formula IV, $R_{3'}$ is selected from the group consisting of methyl, ethyl, n-propyl, iso-propyl, n-butyl, iso-butyl, tert-butyl, halogen, aryl and OR, where R is H, alkyl or aryl; and $R_{5'}$ is selected from the group consisting of hydrogen, methyl, ethyl, n-prpoyl, iso-propyl, n-butyl, iso-butyl, tert-butyl, halogen, aryl and OR, where R is H, alkyl or aryl.

A particularly preferred compound of formula IV is 3-(2-Ethoxybenzylidenyl)-2-indolinone (SU5204).

In a final embodiment, the invention provides compounds having the formula:

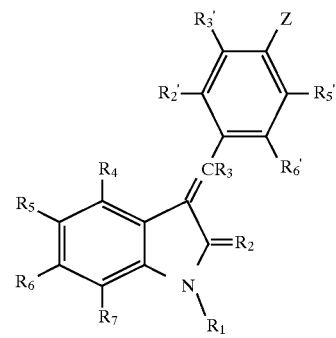

and the pharmaceutically acceptable salts thereof, wherein:

$R_1$ is H or alkyl;

$R_2$ is O or S;

$R_3$ is hydrogen;

$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR';

$R_{2'}$, $R_{3'}$, $R_{5'}$, and $R_{6'}$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR';

n is 0–3;

Z is Br, Cl, F, I, methyl, ethyl, n-propyl, iso-propyl, n-butyl, iso-butyl or tert-butyl;

R is H, alkyl or aryl; and

R' is H, alkyl or aryl.

In a preferred embodiment of the compounds of formula V, $R_{3'}$ is selected from the group consisting of methyl, ethyl, n-propyl, iso-propyl, n-butyl, iso-butyl, tert-butyl, halogen, aryl and OR, where R is H, alkyl or aryl; and $R_{5'}$ is selected from the group consisting of hydrogen, methyl, ethyl, n-propyl, iso-propyl, n-butyl, iso-butyl, tert-butyl, halogen, aryl and OR, where R is H, alkyl or aryl.

A particularly preferred compound of formula V is 3-(4-Bromobenzylidenyl)-2-indolinone (SU4942).

The chemical formulae referred herein may exhibit the phenomena of tautomerism or structural isomerism. For example, the compounds described herein may be adopt a cis or trans conformation about the double bond connecting the indolinone 3-substituent to the indolinone ring, or may be mixtures of cis and trans isomers. As the formulae drawing within this specification can only represent one possible tautomeric or structural isomeric form, it should be understood that the invention encompasses any tautomeric or structural isomeric form, or mixtures thereof, which possesses the ability to regulate, inhibit and/or modulate tyrosine kinase signal transduction or cell proliferation and is not limited to any one tautomeric or structural isomeric form utilized within the formulae drawing.

In addition to the above-described compounds and their pharmaceutically acceptable salts, the invention is further directed, where applicable, to solvated as well as unsolvated forms of the compounds (e.g. hydrated forms) having the ability to regulate and/or modulate cell proliferation.

The compounds described herein may be prepared by any process known to be applicable to the preparation of chemically-related compounds. Suitable processes are illustrated in the examples. Necessary starting materials may be obtained by standard procedures of organic chemistry.

An individual compound's relevant activity and efficacy as an agent to affect receptor tyrosine kinase mediated signal transduction may be determined using available techniques. Preferentially, a compound is subjected to a series of screens to determine the compound's ability to modulate, regulate and/or inhibit cell proliferation. These screens, in the order in which they are conducted, include biochemical assays, cell growth assays and in vivo experiments.

4.4. Indications

The compounds described herein are useful for treating disorders related to unregulated tyrosine kinase signal transduction, including cell proliferative disorders, fibrotic disorders and metabolic disorders.

Cell proliferative disorders which can be treated or further studied by the present invention include cancers, blood vessel proliferative disorders and mesangial cell proliferative disorders.

Blood vessel proliferative disorders refer to angiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration. They also play a pivotal role in cancer development. Other examples of blood vessel proliferation disorders include arthritis, where new capillary blood vessels invade the joint and destroy cartilage, and ocular diseases, like diabetic retinopathy, where new capillaries in the retina invade the vitreous, bleed and cause blindness. Conversely, disorders related to the shrinkage, contraction or closing of blood vessels, such as restenosis, are also implicated.

Fibrotic disorders refer to the abnormal formation of extracellular matrix. Examples of fibrotic disorders include hepatic cirrhosis and mesangial cell proliferative disorders. Hepatic cirrohis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Other fibrotic disorders implicated include atherosclerosis (see, below).

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. The PDGF-R has been implicated in the maintenance of mesangial cell proliferation. Floege et al., 1993, *Kidney International* 43:47S–54S.

PTKs have been associated with such cell proliferative disorders. For example, some members of the RTK family have been associated with the development of cancer. Some of these receptors, like the EGFR (Tuzi et al., 1991, *Br. J. Cancer* 63:227–233; Torp et al., 1992, *APMIS* 100:713–719) HER2/neu (Slamon et al., 1989, *Science* 244:707–712) and the PDGF-R (Kumabe et al., 1992, *Oncogene* 7:627–633) are overexpressed in many tumors and/or persistently activated by autocrine loops. In fact, in the most common and severe cancers these receptor overexpressions (Akbasak and Suner-Akbasak et al., 1992, *J. Neurol. Sci.* 111:119–133; Dickson et al., 1992, *Cancer Treatment Res.* 61:249–273; Korc et al., 1992, *J. Clin. Invest.* 90:1352–1360) and auto-crine loops (Lee and Donoghue, 1992, *J. Cell. Biol.* 118:1057–1070; Korc et al., supra; Akbasak and Suner-Akbasak et al., supra) have been demonstrated. For example, the EGFR receptor has been associated with squamous cell carcinoma, astrocytoma, glioblastoma, head and neck cancer, lung cancer and bladder cancer. HER2 has been associated with breast, ovarian, gastric, lung, pancreas and bladder cancer. The PDGF-R has been associated with glioblastoma, lung, ovarian, melanoma and prostate cancer. The RTK c-met has been generally associated with hepatocarcinogenesis and thus hepatocellular carcinoma. Additionally, c-met has been linked to malignant tumor formation. More specifically, the RTK c-met has been associated with, among other cancers, colorectal, thyroid, pancreatic and gastric carcinoma, leukemia and lymphoma. Additionally, over-expression of the c-met gene has been detected in patients with Hodgkins disease, Burkitts disease, and the lymphoma cell line.

The IGF-IR, in addition to being implicated in nutritional support and in type-II diabetes, has also been associated with several types of cancers. For example, IGF-I has been implicated as an autocrine growth stimulator for several tumor types, e.g. human breast cancer carcinoma cells (Arteaga et al., 1989, *J. Clin. Invest.* 84:1418–1423) and small lung tumor cells (Macauley et al., 1990, *Cancer Res.* 50:2511–2517). In addition, IGF-I, integrally involved in the normal growth and differentiation of the nervous system, appears to be an autocrine stimulator of human gliomas. Sandberg-Nordqvist et al., 1993, *Cancer Res.* 53:2475–2478. The importance of the IGF-IR and its ligands in cell proliferation is further supported by the fact that many cell types in culture (fibroblasts, epithelial cells, smooth muscle cells, T-lymphocytes, myeloid cells, chondrocytes, osteoblasts, the stem cells of the bone marrow) are stimulated to grow by IGF-I. Goldring and Goldring, 1991, *Eukaryotic Gene Expression* 1:301–326. In a series of recent publications, Baserga even suggests that IGF-I-R plays a central role in the mechanisms of transformation and, as such, could be a preferred target for therapeutic interventions for a broad spectrum of human malignancies. Baserga, 1995, *Cancer Res.* 55:249–252; Baserga, 1994, *Cell* 79:927–930; Coppola et al., 1994, *Mol. Cell. Biol.* 14:4588–4595.

The association between abnormalities in RTKs and disease are not restricted to cancer, however. For example, RTKs have been associated with metabolic diseases like psoriasis, diabetes mellitus, wound healing, inflammation, and neurodegenerative diseases. For example, the EGF-R is indicated in corneal and dermal wound healing. Defects in the Insulin-R and the IGF-1R are indicated in type-II diabetes mellitus. A more complete correlation between specific RTKs and their therapeutic indications is set forth in Plowman et al., 1994, *DN&P* 7:334–339.

Not only receptor type tyrosine kinases, but also many cellular tyrosine kinases (CTKs) including src, abl, fps, yes, fyn, lyn, lck, blk, hck, fgr, yrk (reviewed by Bolen et al., 1992, *FASEB J.* 6:3403–3409) are involved in the proliferative and metabolic signal transduction pathway and thus in indications of the present invention. For example, mutated src (v-src) has been demonstrated as an oncoprotein (pp60$^{v-src}$) in chicken. Moreover, its cellular homolog, the proto-oncogene pp60$^{c-src}$ transmits oncogenic signals of many receptors. For example, overexpression of EGF-R or HER2/neu in tumors leads to the constitutive activation of pp60$^{c-src}$, which is characteristic for the malignant cell but absent from the normal cell. On the other hand, mice deficient for the expression of c-src exhibit an osteopetrotic phenotype, indicating a key participation of c-src in osteoclast function and a possible involvement in related disorders. Similarly, Zap 70 is implicated in T-cell signalling.

Furthermore, the identification of CTK modulating compounds to augment or even synergize with RTK aimed blockers is an aspect of the present invention.

Finally, both RTKs and non-receptor type kinases have been connected to hyperimmune disorders.

4.5. Pharmaceutical Formulations And Routes Of Administration

The compounds described herein can be administered to a human patient per se, or in pharmaceutical compositions where it is mixed with suitable carriers or excipient(s). Techniques for formulation and administration of the compounds of the instant application may be found in "Remington's Pharmaceutical Sciences," Mack Publishing Co., Easton, Pa., latest edition.

4.5.1. Routes Of Administration.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

4.5.2. Composition/Formulation.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a co-solvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the PTK modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

4.5.3. Effective Dosage.

Pharmaceutical compositions suitable for use in the present invention include compositions wherein the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the PTK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p.1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

4.5.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition. Suitable conditions indicated on the label may include treatment of a tumor, inhibition of angiogenesis, treatment of fibrosis, diabetes, and the like.

5. EXAMPLE

Compound Synthesis

The compounds of the present invention may be synthesized according to known techniques. The following represent preferred methods for synthesizing the compounds of the claimed invention.

5.1. General Syntheses of 3-Substituted-2-Indolinone Analogs (SU4312 and SU4314 Analogs)

The following general methodologies were used to synthesize 3-substituted-2-indolinone compounds of the invention.

5.1.1. Method A

A reaction mixture of the proper oxindole (2-indolinone) (1 equiv.), the appropriate aldehyde (1.2 equiv.), and piperidine (0.1 equiv.) in ethanol (1–2 mL /1 mmol oxindole) was stirred at 90° C. for 3–5 h. After cooling, the precipitate was filtered, washed with cold ethanol, and dried to yield the target compound.

5.1.2. Method B

Preparation of The Proper Aldehydes via Vilsmeier Reaction. To a solution of N,N-dimethylformamide (1.2 equiv.) in 1,2-dichloroethane (2.0 mL/1.0 mmole of starting material) was added dropwise phosphorus oxychloride (1.2 equiv.) at 0° C. The ice-bath was removed and the reaction mixture was further stirred for 30 min. The proper starting material (1.0 equiv.) was added to the above solution portionwise and the reaction mixture was stirred at 50°–70° C. for 5 h–2 days. The reaction mixture was poured into ice-cold 1N sodium hydroxide solution (pH=9 after mixing) and the resulting mixture was stirred at room temperature for 1 h. The organic layer was separated and the aqueous layer was extracted with ethyl acetate. The combined organic layer was washed with brine until pH=7, dried over anhydrous sodium sulfate and evaporated. The residue was chromatographed on a silica gel column eluting with a solvent mixture of ethyl acetate and hexane to afford the title compound.

Synthesis for 3-Substituted-2-Indolinone Analogs. A reaction mixture of the proper oxindole (2-indolinone) (1 equiv.), the appropriate aldehyde (1.2 equiv.), and piperidine (0.1 equiv.) in ethanol (1–2 mL/1 mmol oxindole) was stirred at 90° C. for 3–5 h. After cooling, the precipitate was filtered, washed with cold ethanol and dried to yield the target compound.

5.2. Synthesis Of 3-Benzylidene-2-Indolinone (SU4928)

The preferred method for synthesizing 3-benzylidene-2-indolinone is as follows: Added 123.2 μl of benzaldehyde and 40 μl of piperidine to a solution of 137.0 mg of oxindole in 2.0 ml methanol. Reflux the reaction mixtured for 3 hours and cool down the mixture in an ice-water bath. Filter the resulting precipitate, wash with cold methanol and dry in an oven at 40° C. overnight. Approximately 129.0 mg of the compound was obtained using such protocol.

5.3. Synthesis Of 3-[(Pyrid-4-yl) methylene]-2-indolinone (SU5212)

The preferred method for synthesizing 3-[(Pyrid-4-yl) methylene]-2-indolinone is as follows: Add 117.0 μl of 4-pyridinecarboxaldehyde and 40 μl of piperidine to a solution of 138.0 mg of oxindole in 2.0 ml methanol. The reaction mixture was refluxed for 3 hours and cooled down in an ice-water bath. The resulting precipitate was filtered, washed with cold methanol and dried in an oven at 40° C. overnight to give 134.5 mg of the compound.

5.4. Synthesis of 3-[4-(morpholin-4-yl)benzylidenyl]-2-indolinone (SU4981) (Method B):

4-(Morpholin-4-yl)benzaldehyde. To a solution of 15 mL of N,N-dimethylformamide in 50 mL of 1,2-dichloroethane was added dropwise 10 mL of phosphorus oxychloride at 0° C. The ice-bath was removed and the reaction mixture was further stirred for 30 min. 4-Phenylmorpholine (16.3 g) was added to the above solution portionwise and the reaction mixture was refluxed for 2 days. Triethylamine (2.5 mL) was added to the above reaction mixture and the reaction was refluxed for 2 days. The reaction mixture was poured into ice-cold 1N sodium hydroxide solution (pH=9 after mixing) and the resulting mixture was stirred at room temperature for 1 h. The organic layer was separated and the aqueous layer was extracted with 2×20 mL of dichloromethane. The combined organic layer was washed with brine until pH=7, dried over anhydrous sodium sulfate and evaporated. The residue was separated on a silica gel column eluting with a solvent mixture of ethyl acetate and hexane to afford 12.95 g (68%) of the title compound as a white solid.

3-[4-(Morpholin-4-yl)benzylidenyl]-2-indolinone (SU4981). A reaction mixture of 6.66 g of oxindole, 11.50 g of the 4-(morpholine-4-yl)benzaldehyde, and 5 mL of piperidine in 50 mL of ethanol was stirred at 90° C. for 5 h. After cooling, the precipitate was filtered, washed with cold ethanol, and dried to yield 15.0 g (98%) of the title compound as a yellow solid.

5.5. Synthesis of 3-[4-(4-Formylpiperazin-1-yl) benzylidenyl]-2-indolinone (SU4984) (Method B):

4-(4-Formylpiperazin-1-yl)benzaldehyde. To a solution of 3.9 mL (30 mmoles) of N,N-dimethylformamide in 20 mL of 1,2-dichloroethane was added dropwise 3.0 mL (3.9 mmoles) of phosphorus oxychloride at 0° C. The ice-bath was removed and the reaction mixture was further stirred for 15 min. 1-Phenylpiperazine (16.0 g, 10 mmoles) was added to the above solution portionwise and the reaction mixture was stirred at 50° C. for 1 h. The reaction mixture was poured into ice-cold 1N sodium hydroxide solution and stirred at room temperature for 1 h. The organic layer was separated and the aqueous layer was extracted with 2×20 mL of ethyl acetate. The combined organic layer was washed with brine until pH=7, dried over anhydrous sodium sulfate and evaporated. The residue was separated on a silica gel column eluting with a mixture of ethyl acetate and hexane to afford 9.0 g (41%) of the title compound a light yellow solid.

3-[4-(4-Formylpiperazin-1-yl)benzylidenyl]-2-indolinone (SU4984). A reaction mixture of 133.15 mg of oxindole, 228.3 mg of 4-(piperazin-lyl)benzaldehyde, and 3 drops of piperidine in 2 mL of ethanol was stirred at 90° C. for 5 h. After cooling, the precipitate was filtered, washed with cold ethanol and dried to yield 199.5 mg (65%) of the title compound a yellow solid.

5.6. Synthesis of 3-[4-(Piperidin-1-yl)benzylidenyl]-2-indolinone (SU5450) (Method B).

4-(Piperidin-1-yl)benzaldehyde. To a solution of 2.3 mL (30 mmoles) of N,N-dimethylformamide in 10 mL of 1,2-dichloroethane was added dropwise 2.8 mL (30 mmoles) of phosphorus oxychloride at 0° C. The ice-bath was removed and the reaction mixture was stirred for 15 min. 1-Phenylpiperidine (3.2 mL, 20 mmoles) was added to the above solution portionwise and the reaction mixture was refluxed overnight. The reaction mixture was poured into ice-cold 2N sodium hydroxide solution and stirred at room temperature for 1 h. The organic layer was separated and the aqueous layer was extracted with 2×20 mL of ethyl acetate. The combined organic layer was washed with brine until pH=7, dried over anhydrous sodium sulfate and evaporated.

The residue was separated on a silica gel column eluting with ethyl acetate and hexane to afford 1.5 g (40%) of the title compound as a white solid.

3-[4-(Piperidin-1-yl)benzylidenyl]-2-indolinone (SU5450). A reaction mixture of 134.0 mg of oxindole, 226.8 g of 4-(piperidine-1-yl)benzaldehyde, and 3 drops of piperidine in 2 mL of ethanol was stirred at 90° C. for 5 h. After cooling, the precipitate was filtered, washed with cold ethanol, and dried to yield 268.5 mg (88%) of the title compound as a yellow solid.

5.7. Synthesis of 3-[2-Chloro-4-methoxybenzylidenyl]-2-indolinone (SU5480).

2-Chloro-4-methoxybenzaldehyde. The reaction mixture of 1.0 g (6.4 mmoles) of 2-chloro-4-hydroxybenzaldehyde, 4.4 g (32 mmoles) of potassium carbonate, and 1.4 g (9.6 mmoles) of methyl iodide in 10 mL of N,N-dimethylformamide was stirred at 70° C. for 2 h and poured into ice water. The precipitate was filtered, washed with water, and dried at 40° C. in vacuum oven overnight to yield 750 mg (68%) of the title compound as a light pink solid.

3-[2-Chloro-4-methoxybenzylidenyl]-2-indolinone (SU5480). The reaction mixture of 487.9 mg (3.7 mmoles) of oxindole, 750 mg (4.3 mmoles) of 2-chloro-4-methoxybenzaldehyde and 4 drops of piperidine in 5 mL of ethanol was heated to 90° C. for 2 h and cooled to room temperature. The yellow precipitate was filtered, washed with cold ethanol, and dried at 40° C. in a vacuum oven overnight to give 680.2 mg (62%) of the title compound.

5.8. Synthesis of 3-[(4-Methylthien-2-yl)methylene]-2-indolinone (SU5401).

A reaction mixture of 133.0 mg of oxindole, 151.2 mg of the 4-methylthiophene-2-carboxaldehyde, and 3 drops of piperidine in 3 mL of ethanol was stirred at 90° C. for 3 h. After cooling, the precipitate was filtered, washed with cold ethanol, and dried to yield 147.3 mg (61%) of the title compound as a yellow solid.

5.9. Synthesis of 3-[(3-Methylpyrrol-2-yl)methylene]-2-indolinone (SU5404).

A reaction mixture of 133.0 mg of oxindole, 130.9 mg of the 3-methylpyrrole-2-carboxaldehyde, and 3 drops of piperidine in 2 mL of ethanol was stirred at 90° C. for 3 h. After cooling, the precipitate was filtered, washed with cold ethanol, and dried to yield 150.9 mg (67%) of the title compound as a yellow solid.

5.10. Synthesis of 3-[(3,4-Dimethylpyrrol-2-yl)methylene]-2-indolinone (SU5406)

3-[(3,4-Dimethylpyrrol-2-yl)methylene]-2-indolinone was synthesized as described in *J. Heterocyclic Chem.* 13:1145–1147 (1976).

Ethyl 4-methylpyrrol-3-carboxylate. A solution of 11.86 g (0.1 moles) of ethyl crotonate and 19.50 g (0.1 moles) of ρ-toluenesulfonylmethylisocyanide in 500 mL of a 2:1 ether/dimethylsulfoxide was added dropwise into a suspension of 6.8 g of sodium hydride (60% mineral oil dispension, 0.17 moles) in ether at room temperature. Upon completion of addition the reaction mixture was stirred for 30 min and diluted with 400 mL of water. The aqueous layer was extracted with 3×100 mL of ether. The combined ether extracts were passed through a column of alumina eluting with dichloromethane. The organic solvent was evaporated and the resulting residue was solidified on standing. The solid was washed with hexane and dried at 40° C. in vacuum oven overnight to yield 12.38 g (80%) of the title compound.

Preparation of 3,4-Dimethylpyrrole. To a solution of 23 g (80 mmoles) of sodium dihydrobis(2-methoxyethoxy aluminate) was added dropwise of a solution of 5 g (34 mmoles) of ethyl 4-methylpyrrol-3-carboxylate in 50 mL of benzene at room temperature under nitrogen atmosphere. The reaction mixture was stirred for 18 h. Water (100 mL) was added to the reaction mixture. The organic layer was separated, washed with brine and dried over anhydrous sodium sulfate. The solvent was removed and the residue was distilled giving 1.2g (44%) of the title compound.

Preparation of 3,4-Dimethylpyrrole-2-carboxaldehyde. To a solution of 0.92 mL (12 mmoles) of N,N-dimethylformamide in 10 mL of 1,2-dichloroethane was added dropwise 1.0 mL (12 mmoles) of phosphorus oxychloride at 0° C. The ice-bath was removed and the reaction mixture was further stirred for 30 min. 3,4-Dimethylpyrrole (960.0 mg, 10 mmoles) was added to the above solution portionwise and the reaction mixture was stirred at 50° C. for 5 h. The reaction mixture was poured into ice-cold 1N sodium hydroxide solution (pH=9 after mixing) and the resulting mixture was stirred at room temperature for 1 h. The organic layer was separated and the aqueous layer was extracted with ethyl acetate. The combined organic layer was washed with brine until pH=7, dried over anhydrous sodium sulfate and evaporated. The residue was chromatographed on a silica gel column eluting with a solvent mixture of ethyl acetate and hexane to afford 610 mg (50%) of the title compound.

3-[(3,4-Dimethylpyrrol-2-yl)methylene]-2-indolinone (SU5406). A reaction mixture of 67.0 mg (0.5 mmoles) of oxindole, 73.0 mg (0.6 mmoles) of the 3,4-dimethylpyrrole-2-carboxaldehyde, and 2 drops of piperidine in 2 mL of ethanol was stirred at 90° C. for 3 h. After cooling, the precipitate was filtered, washed with cold ethanol, and dried to yield 87.7 mg (37%) of the title compound as a yellow solid.

5.11. Synthesis of 3-[(2,4-Dimethyl-3-ethoxycarbonylpyrrol-5-yl methylene]-2-indolinone (SU5408)

A reaction mixture of 134.0 mg of oxindole, 234.3 mg of the 4-ethoxycarbonyl-3,5-dimethylpyrrole-2-carboxaldehyde, and 3 drops of piperidine in 3 mL of ethanol was stirred at 90° C. for 3 h. After cooling, the precipitate was filtered, washed with cold ethanol, and dried to yield 244.6 mg (79%) of the title compound as a yellow solid.

5.12. Synthesis of 3-[(2,4-Dimethylpyrrol-5-yl)methylene]-2-indolinone (SU5416)

A reaction mixture of 134.0 mg of oxindole, 147.8 mg of the 3,5-dimethylpyrrole-2-carboxaldehyde, and 3 drops of piperidine in 2 mL of ethanol was stirred at 90° C. for 3 h. After cooling, the precipitate was filtered, washed with cold ethanol, and dried to yield 136.7 mg (57%) of the title compound as a yellow solid.

5.13. Synthesis of 3-[(2-Methylmercaptothien-5-yl) methylene]-2-indolinone (SU5419)

A reaction mixture of 134.0 mg of oxindole, 189.9 mg of the 5-methylmercaptothiophene-2-carboxaldehyde, and 3 drops of piperidine in 2 mL of ethanol was stirred at 90° C. for 3 h. After cooling, the precipitate was filtered, washed with cold ethanol, and dried to yield 246.6 mg (90%) of the title compound as a orange solid.

5.14. Synthesis of 3-[(2-Methylthien-5-yl)methylene]-2-indolinone (SU5424)

A reaction mixture of 134.0 mg of oxindole, 151.42 mg of the 5-methylthiophene-2-carboxaldehyde, and 3 drops of piperidine in 2 mL of ethanol was stirred at 90° C. for 3 h. After cooling, the precipitate was filtered, washed with cold ethanol, and dried to yield 237.8 mg (99%) of the title compound as a yellow solid.

5.15. Synthesis of 3-[(3-Methylthien-2-yl)methylene]-2-indolinone (SU5427)

A reaction mixture of 134.0 mg of oxindole, 151.4 mg of the 3-methylthiophene-2-carboxaldehyde, and 3 drops of piperidine in 2 mL of ethanol was stirred at 90° C. for 3 h. After cooling, the precipitate was filtered, washed with cold ethanol, and dried to yield 157.8 mg (65%) of the title compound as a yellow solid.

5.16. Synthesis of 3-(2,5-Dimethoxybenzylidenyl)-2-indolinone (SU4793)

3-(2,5-Dimethoxybenzylidenyl)-2-indolinone is synthesized according to Method A.

5.17. Synthesis of 3-(2,3-dimethoxybenzylidenyl)-2-indolinone (SU4794)

3-(2,3-dimethoxybenzylidenyl)-2-indolinone is synthesized according to Method A.

5.18. Synthesis of 3-(3-bromo-6-methoxybenzylidenyl)-2-indolinone (SU4796)

3-(3-bromo-6-methoxybenzylidenyl)-2-indolinone is synthesized according to Method A.

5.19. Synthesis of 3-[4-(4-t-butylcarbonyl-piperazin-1-yl)benzylidenyl]-2-indolinone (SU5393)

3-[4-(4-t-butylcarbonyl-piperazin-1-yl)benzylidenyl]-2-indolinone is synthesized according to Method B.

5.20. Synthesis of 3-[(furan-2-yl)methylene]-2-indolinone (SU4798)

3-[(furan-2-yl)methylene]-2-indolinone is synthesized according to Method A.

5.21. Synthesis of 3-(4-acetamidobenzylidenyl)-2-indolinone (SU4799)

3-(4-acetamidobenzylidenyl)-2-indolinone is synthesized according to Method A.

5.22. Synthesis of 3-(2-chloro-4-hydroxybenzylidenyl)-2-indolinone (SU4932)

3-(2-chloro-4-hydroxybenzylidenyl)-2-indolinone is synthesized according to Method A.

5.23. Synthesis of 3-(4-Bromobenzylidenyl)-2-indolinone (SU4942)

3-(4-Bromobenzylidenyl)-2-indolinone is synthesized according to Method A.

5.24. Synthesis of 3-(4-Acetylaminobenzylidenyl)-2-indolinone (SU4944)

3-(4-Acetylaminobenzylidenyl)-2-indolinone is synthesized according to Method A.

5.25. Synthesis of 3-(2-Methoxybenzylidenyl)-2-indolinone (SU4949)

3-(2-Methoxybenzylidenyl)-2-indolinone is synthesized according to Method A.

5.26. Synthesis of 3-(4-Dimethylaminobenzylidenyl)-1-methyl-2-indolinone (SU4952)

3-(4-Dimethylaminobenzylidenyl)-1-methyl-2-indolinone is synthesized according to Method A.

5.27. Synthesis of 3-(4-Dimethylaminobenzylidenyl)-2-indolinone (SU4312)

3-(4-Dimethylaminobenzylidenyl)-2-indolinone is available from Maybridge Chemical Co. Ltd.

5.28. Synthesis of 3-(4-Bromobenzylidenyl)-1-methyl-2-indolinone (SU4956)

3-(4-Bromobenzylidenyl)-1-methyl-2-indolinone is thesized according to Method A.

5.29. Synthesis of 5-Chloro-3-(4-dimethylaminobenzylidenyl)-2-indolinone (SU4967)

5-Chloro-3-(4-dimethylaminobenzylidenyl)-2-indolinone is synthesized according to Method A.

5.30. Synthesis of 3-(4-Bromobenzylidenyl)-5-chloro-2-indolinone (SU4972)

3-(4-Bromobenzylidenyl)-5-chloro-2-indolinone is synthesized according to Method A.

5.31. Synthesis of 3-(4-Diethylaminobenzylidenyl)-2-indolinone (SU4978)

3-(4-Diethylaminobenzylidenyl)-2-indolinone is synthesized according to Method A.

5.32. Synthesis of 3-(4-Di-n-butylaminobenzylidenyl)-2-indolinone (SU4979)

3-(4-Di-n-butylaminobenzylidenyl)-2-indolinone is synthesized according to Method A.

5.33. Synthesis of 1-Methyl-3-[4-(morpholin-4-yl)benzylidenyl]-2-indolinone (SU4982)

1-Methyl-3-[4-(morpholin-4-yl)benzylidenyl]-2-indolinone is synthesized according to Method B.

5.34. Synthesis of 5-Chloro-3-(4-(morpholine-4-yl)benzylidenyl)-2-indolinone (SU4983)

5-Chloro-3-(4-(morpholine-4-yl)benzylidenyl)-2-indolinone is synthesized according to Method B.

5.35. Synthesis of 3-(3,4-Dichlorobenzylidenyl)-2-indolinone (SU5201)

3-(3,4-Dichlorobenzylidenyl)-2-indolinone is synthesized according to Method A.

5.36. Synthesis of 3-(2-Ethoxybenzylidenyl]-2-indolinone (SU5204)

3-(2-Ethoxybenzylidenyl]-2-indolinone is synthesized according to Method A.

5.37. Synthesis of 3-(4-Fluorobenzylidenyl)-2-indolinone (SU5205)

3-(4-Fluorobenzylidenyl)-2-indolinone is synthesized according to Method A.

5.38. Synthesis of 3-[(Thien-2-yl)methylene]-2-indolinone (SU5208)

3-[(Thien-2-yl)methylene]-2-indolinone is synthesized according to Method A.

5.39. Synthesis of 3-(2-Methoxybenzylidenyl)-2-indolinone (SU5214)

3-(2-Methoxybenzylidenyl)-2-indolinone is synthesized according to Method A.

5.40. Synthesis of 3-[2-[3,5-Di-(trifluoromethyl)phenyl]furan-5-yl]methylene]-2 -indolinone (SU5217)

3-[2-[3,5-Di-(trifluoromethyl)phenyl]furan-5-yl]methylene]-2 -indolinone is synthesized according to Method A.

5.41. Synthesis of 2,6-Di-(dimethylamino)-3,5-di-[(indolin-2-one-3-ylidenyl)met hyl]-phenylcyanide (SU5218)

2,6-Di-(dimethylamino)-3,5-di-[(indolin-2-one-3-ylidenyl)met hyl]-phenylcyanide is synthesized according to Method A.

5.42. Synthesis of 3-[(3-(2-carboxyethyl)-4-methylpyrrol-5-yl)methylene]-2-indo linone (SU5402)

3-[(3-(2-carboxyethyl)-4-methylpyrrol-5-yl) methylene]-2-indo linone is synthesized according to Method A.

5.43. Synthesis of 3-[(3,4-Dibromo-5-methylpyrrol-2-yl)methylene]-2-indolinone (SU5403)

3-[(3,4-Dibromo-5-methylpyrrol-2-yl)methylene]-2-indolinone is synthesized according to Method B.

5.44. Synthesis of 3-[(3,4-Dimethyl-2-formylpyrrole-5-yl)methylene)-2-indolinone (SU5405)

3-[(3,4-Dimethyl-2-formylpyrrole-5-yl)methylene]-2-indolinone is synthesized according to Method A.

5.45. Synthesis of 3-{[4-(2-methoxycarbonylethyl)-3-methylpyrrol-5-yl]methylene}-2-indolinone (SU5407)

3-{[4-(2-methoxycarbonylethyl)-3-methylpyrrol-5-yl]methylene}-2-indolinone is synthesized according to Method A.

5.46. Synthesis of 3-[2-Iodofuran-5-yl)methylene]-2-indolinone (SU5409)

3-[2-Iodofuran-5-yl)methylene]-2-indolinone is synthesized according to Method A.

5.47. Synthesis of 3-[(3-Ethoxycarbonyl-2-methylfuran-5-yl)methylene]-2-indolin one (SU5410)

3-[(3-Ethoxycarbonyl-2-methylfuran-5-yl)methylene]-2-indolinone is synthesized according to Method A.

5.48. Synthesis of 3-[(3-Bromothiene-2-yl)methylene]-2-indolinone (SU5418)

3-[(3-Bromothiene-2-yl)methylene]-2-indolinone is synthesized according to Method A.

5.49. Synthesis of 3-[(2-Chlorothiene-5-yl)methylene)-2-indolinone (SU5420)

3-[(2-Chlorothiene-5-yl)methylene)-2-indolinone is synthesized according to Method A.

5.50. Synthesis of 3-[(2,3-Dimethylfuran-5-yl)methylene]-2-indolinone (SU5421)

3-[(2,3-Dimethylfuran-5-yl)methylene]-2-indolinone is synthesized according to Method A.

5.51. Synthesis of 3-[(5-Nitrothien-2-yl)methylene]-2-indolinone (SU5422)

3-[(5-Nitrothien-2-yl)methylene]-2-indolinone is synthesized according to Method A.

5.52. Synthesis of 3-[(2-Carboxythien-5-yl)methylene]-2-indolinone (SU5423)

3-[(2-Carboxythien-5-yl)methylene]-2-indolinone is synthesized according to Method A.

5.53. Synthesis of 3-[(2-Bromothiene-5-yl)methylene]-2-indolinone (SU5425)

3-[(2-Bromothiene-5-yl)methylene]-2-indolinone is synthesized according to Method A.

5.54. Synthesis of 3-[(4-Bromothiene-2-yl)methylene]-2-indolinone (SU5426)

3-[(4-Bromothiene-2-yl)methylene]-2-indolinone is synthesized according to Method A.

5.55. Synthesis of 3-[(2-Sulphonylfuran-5-yl)methylene]-2-indolinone sodium salt (SU5428)

3-[(2-Sulphonylfuran-5-yl)methylene]-2-indolinone sodium salt is synthesized according to Method A.

5.56. Synthesis of 3-[(Furan-2-yl)methylene]-2-indolinone (SU5429)

3-[(Furan-2-yl)methylene]-2-indolinone is synthesized according to Method A.

5.57. Synthesis of 3-[(2-Methylfuran-5-yl)methylene]-2-indolinone (SU5430)

3-[(2-Methylfuran-5-yl)methylene]-2-indolinone is synthesized according to Method A.

5.58. Synthesis of 3-[(2-Ethylfuran-5-yl)methylene-2-indolinone (SU5431)

3-[(2-Ethylfuran-5-yl)methylene-2-indolinone is synthesized according to Method A.

5.59. Synthesis of 3-[(2-Nitrofuran-5-yl)methylene]-2-indolinone (SU5432)

3-[(2-Nitrofuran-5-yl)methylene]-2-indolinone is synthesized according to Method A.

5.60. Synthesis of 3-[(5-Bromofuran-2-yl)methylene]-2-indolinone (SU5438)

3-[(5-Bromofuran-2-yl)methylene]-2-indolinone is synthesized according to Method A.

5.61. Synthesis of 3-[(2-Ethylthien-5-yl)methylene]-2-indolinone (SU5451)

3-[(2-Ethylthien-5-yl)methylene]-2-indolinone is synthesized according to Method A.

5.62. Synthesis of 3-[(4,5-Dimethyl-3-ethylpyrrol-2-yl)methylene]-2-indolinone (SU5453)

3-[(4,5-Dimethyl-3-ethylpyrrol-2-yl)methylene]-2-indolinone is synthesized according to Method A.

5.63. Synthesis of 3-[(5-Ethoxycarbonyl-4-ethoxycarbonylethyl-3-ethoxycarbonylm ethylpyrrol-2-yl)methylene]-2-indolinone (SU5454)

3-[(5-Ethoxycarbonyl-4-ethoxycarbonylethyl-3-ethoxycarbonylm ethylpyrrol-2-yl)methylene]-2-indolinone is synthesized according to Method A.

5.64. Synthesis of 3-[(5-Carboxy-3-ethyl-4-methylpyrrol-2-yl)methylene]-2-indolinone (SU5455)

3-[(5-Carboxy-3-ethyl-4-methylpyrrol-2-yl)methylene]-2-indolinone is synthesized according to Method A.

5.65. Synthesis of 3-[(3,5-Diiodo-4-methylpyrrol-2-yl)methylene]-2-indolinone (SU5456)

3-[(3,5-Diiodo-4-methylpyrrol-2-yl)methylene]-2-indolinone is synthesized according to Method A.

5.66. Synthesis of 3-[(5-Chloro-3-methoxycarbonyl-4-methoxycarbonylmethylpyrrol -2-yl) methylene]-2-indolinone (SU5459)

3-[(5-Chloro-3-methoxycarbonyl-4-methoxycarbonylmethylpyrrol -2-yl)methylene]-2-indolinone is synthesized according to Method A.

5.67. Synthesis of 3-[(3-Acetyl-5-ethoxycarbonyl-4-methylpyrrol)-2-yl)methylene ]-2-indolinone (SU5460)

3-[(3-Acetyl-5-ethoxycarbonyl-4-methylpyrrol)-2-yl)methylene]-2-indolinone is synthesized according to Method A.

5.68. Synthesis of 3-{[1-(3,5-Dichlorophenyl) pyrrol-2-yl]methylene}-2-indolinone (SU5461)

3-{[1-(3,5-Dichlorophenyl)pyrrol-2-yl]methylene}-2-indolinone is synthesized according to Method A.

5.69. Synthesis of 3-[1-(4-Chlorophenyl)pyrrol-2-yl)methylene]-2-indolinone (SU5462)

3-[1-(4-Chlorophenyl)pyrrol-2-yl)methylene]-2-indolinone is synthesized according to Method A.

5.70. Synthesis of 3-[(4-Ethoxycarbonyl-3-methyl)pyrrol-2-yl)methylene]-2-indolinone (SU5463)

3-[(4-Ethoxycarbonyl-3-methyl)pyrrol-2-yl)methylene]-2-indolinone is synthesized according to Method A.

5.71. Synthesis of 3-[(1-Methylpyrrol-2-yl)methylene]-2-indolinone (SU5464)

3-[(1-Methylpyrrol-2-yl)methylene]-2-indolinone is synthesized according to Method A.

5.72. Synthesis of 3-[(5-Ethoxycarbonyl-3-ethoxycarbonylethyl-4-ethoxylcarbonyl methylpyrrol-2-yl)methylene]-2-indolinone (SU5465)

3-[(5-Ethoxycarbonyl-3-ethoxycarbonylethyl-4-ethoxylcarbonyl methylpyrrol-2-yl)methylene]-2-indolinone is synthesized according to Method A.

5.73. Synthesis of 3-[4-(Pyrrolidin-1-yl)benzylidenyl]-2-indolinone (SU5466)

3-[4-(Pyrrolidin-1-yl)benzylidenyl]-2-indolinone is synthesized according to Method A.

5.74. Synthesis of 3-[(5-Methylimidazol-2-yl)methylene]-2-indolinone (SU5468)

3-[(5-Methylimidazol-2-yl)methylene]-2-indolinone is synthesized according to Method A.

5.75. Synthesis of 3-[(5-Methylthiazol-2-yl)methylene]-2-indolinone (SU5469)

3-[(5-Methylthiazol-2-yl)methylene]-2-indolinone is synthesized according to Method A.

5.76. Synthesis of 3-[(3-Methylpyrazol-5-yl)methylene]-2-indolinone (SU5472)

3-[(3-Methylpyrazol-5-yl)methylene]-2-indolinone is synthesized according to Method A.

5.77. Synthesis of 3-[(Imidazol-4-yl)methylene]-2-indolinone (SU5473)

3-[(Imidazol-4-yl)methylene]-2-indolinone is synthesized according to Method A.

5.78. Synthesis of 3-[(4-Chloropyrazol-3-yl)methylene]-2-indolinone (SU5474)

3-[(4-Chloropyrazol-3-yl)methylene]-2-indolinone is synthesized according to Method A.

5.79. Synthesis of 3-[(4-Bromo-1-(4-chlorobenzyl)pyrazol-5-yl)methylene]-2-indo linone (SU5475)

3-[(4-Bromo-1-(4-chlorobenzyl)pyrazol-5-yl) methylene]-2-indolinone is synthesized according to Method A.

5.80. Synthesis of 3-[(4-Chloro-1-methylpyrazol-3-yl)methylene]-2-indolinone (SU5476)

3-[(4-Chloro-1-methylpyrazol-3-yl)methylene]-2-indolinone is synthesized according to Method A.

5.81. Synthesis of 3-[(4-Ethyl-3,5-dimethylpyrrol-2-yl)methylene]-2-indolinone (SU5477)

3-[(4-Ethyl-3,5-dimethylpyrrol-2-yl)methylene]-2-indolinone is synthesized according to Method B.

5.82. Synthesis of 3-[(5-Ethylpyrrol-2-yl)methylene]-2-indolinone (SU5478)

3-[(5-Ethylpyrrol-2-yl)methylene]-2-indolinone is synthesized according to Method B.

5.83. Synthesis of 3-[3,5-Dimethyl-4-(propen-2-yl)pyrrol-2-yl)methylene]-2-indolinone (SU5479)

3-[3,5-Dimethyl-4-(propen-2-yl)pyrrol-2-yl) methylene]-2-indolinone is synthesized according to Method B.

5.84. Synthesis of 5,6-Dimethoxyl-3-[2,3-dimethoxylbenzylidenyl]-2-indolinone (SU5495)

5,6-Dimethoxyl-3-[2,3-dimethoxylbenzylidenyl]-2-indolinone is synthesized according to Method A.

5.85. Synthesis of 3-[2,4,6-Trimethoxybenzylidenyl]-2-indolinone (SU5607)

3-[2,4,6-Trimethoxybenzylidenyl]-2-indolinone is synthesized according to Method A.

5.86. Synthesis of 5-Chloro-3-[(pyrrol-2-yl)methylene]-2-indolinone (SU5612)

5-Chloro-3-[(pyrrol-2-yl)methylene]-2-indolinone is synthesized according to Method A.

5.87. Synthesis of 5-Chloro-3-[(3-methylpyrrol-2-5 yl)methylene]-2-indolinone (SU5613)

5-Chloro-3-[(3-methylpyrrol-2-yl)methylene]-2-indolinone is synthesized according to Method A.

5.88. Synthesis of 3-(4-isopropylbenzylidenyl)-2-indolinone (SU4313)

3-(4-isopropylbenzylidenyl)-2-indolinone is available from Maybridge Chemical Co. Ltd.

5.89. Synthesis of 5-Chloro-3-[(3,5-dimethylpyrrol-2-yl)methylene]-2-indolinone (SU5614)

5-Chloro-3-[(3,5-dimethylpyrrol-2-yl)methylene]-2-indolinone is synthesized according to Method A.

5.90. Synthesis of 3-[(pyrrol-2-yl)methylene]-2-indolinone (SU4314)

3-[(pyrrol-2-yl)methylene]-2-indolinone is available from Maybridge Chemical Co. Ltd.

5.91. Synthesis of 5-Chloro-3-[(indol-3-yl)methylene]-2-indolinone (SU5615)

5-Chloro-3-[(indol-3-yl)methylene]-2-indolinone is synthesized according to Method A.

5.92. Synthesis of 5-Chloro-3-[(thien-2-yl)methylene]-2-indolinone (SU5616)

5-Chloro-3-[(thien-2-yl)methylene]-2-indolinone is synthesized according to Method A.

5.93. Synthesis of 5-Chloro-3-[(3-methylthien-2-yl)methylene]-2-indolinone (SU5617)

5-Chloro-3-[(3-methylthien-2-yl)methylene]-2-indolinone is synthesized according to Method A.

5.94. Synthesis of 5-Chloro-3-[(5-methylthien-2-yl)methylene]-2-indolinone (SU5618)

5-Chloro-3-[(5-methylthien-2-yl)methylene]-2-indolinone is synthesized according to Method A.

5.95. Synthesis of 5-Chloro-3-[(5-ethylthien-2-yl)methylene]-2-indolinone (SU5619)

5-Chloro-3-[(5-ethylthien-2-yl)methylene]-2-indolinone is synthesized according to Method A.

5.96. Synthesis of 5-Chloro-3-[(5-methylmercaptothien-2-yl)methylene]-2-indolinone (SU5620)

5-Chloro-3-[(5-methylmercaptothien-2-yl)methylene]-2-indolinone is synthesized according to Method A.

5.97. Synthesis of 5-Chloro-3-[(imidazol-2-yl)methylene]-2-indolinone (SU5621)

5-Chloro-3-[(imidazol-2-yl)methylene]-2-indolinone is synthesized according to Method A.

5.98. Synthesis of 3-[2,4-Dimethoxy-6-methylbenzylidenyl]-2-indolinone (SU5623)

3-[2,4-Dimethoxy-6-methylbenzylidenyl]-2-indolinone is synthesized according to Method A.

5.99. Synthesis of 5-Nitro-3-[(pyrrol-2-yl)methylene]-2-indolinone (SU5624)

5-Nitro-3-[(pyrrol-2-yl)methylene]-2-indolinone is synthesized according to Method A.

5.100. Synthesis of 3-[(3-Methylpyrrol-2-yl)methylene]-5-nitro-2-indolinone (SU5625)

3-[(3-Methylpyrrol-2-yl)methylene]-5-nitro-2-indolinone is synthesized according to Method A.

5.101. Synthesis of 3-[(3,5-Dimethylpyrrol-2-yl)methylene]-5-nitro-2-indolinone (SU5626)

3-[(3,5-Dimethylpyrrol-2-yl)methylene]-5-nitro-2-indolinone is synthesized according to Method A.

5.102. Synthesis of 3-[(Indol-3-yl)methylene]-5-nitro-2-indolinone (SU5627)

3-[(Indol-3-yl)methylene]-5-nitro-2-indolinone is synthesized according to Method A.

5.103. Synthesis of 5-Nitro-3-[(thien-2-yl)methylene]-2-indolinone (SU5628)

5-Nitro-3-[(thien-2-yl)methylene]-2-indolinone is synthesized according to Method A.

5.104. Synthesis of 3-[(3-Methylthien-2-yl)methylene]-5-nitro-2-indolinone (SU5629)

3-[(3-Methylthien-2-yl)methylene]-5-nitro-2-indolinone is synthesized according to Method A.

5.105. Synthesis of 3-[(5-Methylthien-2-yl)methylene]-5-nitro-2-indolinone (SU5630)

3-[(5-Methylthien-2-yl)methylene]-5-nitro-2-indolinone is synthesized according to Method A.

5.106. Synthesis of 3-[(5-Ethylthien-2-yl)methylene]-5-nitro-2-indolinone (SU5631)

3-[(5-Ethylthien-2-yl)methylene]-5-nitro-2-indolinone is synthesized according to Method A.

5.107. Synthesis of 3-[(5-Methylmercaptothien-2-yl)methylene]-5-nitro-2-indolinone (SU5632)

3-[(5-Methylmercaptothien-2-yl)methylene]-5-nitro-2-indolinone is synthesized according to Method A.

5.108. Synthesis of 3-[(Imidazol-2-yl)methylene]-5-nitro-2-indolinone (SU5633)

3-[(Imidazol-2-yl)methylene]-5-nitro-2-indolinone is synthesized according to Method A.

5.109. Synthesis of 3-[(Oxazol-2-yl)methylene]-2-indolinone (CS7127)

3-[(Oxazol-2-yl)methylene]-2-indolinone is synthesized according to Method A.

5.110. Synthesis of 3-[(Oxazol-4-yl)methylene]-2-indolinone (CS7128)

3-[(Oxazol-4-yl)methylene]-2-indolinone is synthesized according to Method A.

5.111. Synthesis of 3-[(Oxazol-5-yl)methylene]-2-indolinone (CS7129)

3-[(Oxazol-5-yl)methylene]-2-indolinone is synthesized according to Method A.

5.112. Synthesis of 3-[(Thiazol-2-yl)methylene]-2-indolinone (CS7130)

3-[(Thiazol-2-yl)methylene]-2-indolinone is synthesized according to Method A.

5.113. Synthesis of 3-[(Thiazol-4-yl)methylene]-2-indolinone (CS7131)

3-[(Thiazol-4-yl)methylene]-2-indolinone is synthesized according to Method A.

5.114. Synthesis of 3-[(Thiazol-5-yl)methylene]-2-indolinone (CS7132)

3-[(Thiazol-5-yl)methylene]-2-indolinone is synthesized according to Method A.

5.115. Synthesis of 3-[(Imidazol-2-yl)methylene]-2-indolinone (CS7133)

3-[(Imidazol-2-yl)methylene]-2-indolinone is synthesized according to Method A.

5.116. Synthesis of 3-[(Pyrazol-3-yl)methylene]-2-indolinone (CS7135)

3-[(Pyrazol-3-yl)methylene]-2-indolinone is synthesized according to Method A.

5.117. Synthesis of 3-[(Pyrazol-4-yl)methylene]-2-indolinone (CS7136)

3-[(Pyrazol-4-yl)methylene]-2-indolinone is synthesized according to Method A.

5.118. Synthesis of 3-[(Isoxazol-3-yl)methylene]-2-indolinone (CS7137)

3-[(Isoxazol-3-yl)methylene]-2-indolinone is synthesized according to Method A.

5.119. Synthesis of 3-[(Isoxazol-4-yl)methylene]-2-indolinone (CS7138)

3-[(Isoxazol-4-yl)methylene]-2-indolinone is synthesized according to Method A.

5.120. Synthesis of 3-[(Isoxazol-5-yl)methylene]-2-indolinone (CS7139)

3-[(Isoxazol-5-yl)methylene]-2-indolinone is synthesized according to Method A.

5.121. Synthesis of 3-[(Isothiazol-3-yl)methylene]-2-indolinone (CS7140)

3-[(Isothiazol-3-yl)methylene]-2-indolinone is synthesized according to Method A.

5.122. Synthesis of 3-[(Isothiazol-4-yl)methylene]-2-indolinone (CS7141)

3-[(Isothiazol-4-yl)methylene]-2-indolinone is synthesized according to Method A.

5.123. Synthesis of 3-[(Isothiazol-5-yl)methylene]-2-indolinone (CS7142)

3-[(Isothiazol-5-yl)methylene]-2-indolinone is synthesized according to Method A.

5.124. Synthesis of 3-[(1,2,3-Triazol-4-yl)methylene]-2-indolinone (CS7143)

3-[(1,2,3-Triazol-4-yl)methylene]-2-indolinone is synthesized according to Method A.

5.125. Synthesis of 3-[(1,3,4-Thiadiazol-2-yl)methylene]-2-indolinone (CS7144)

3-[(1,3,4-Thiadiazol-2-yl)methylene]-2-indolinone is synthesized according to Method A.

5.126. Synthesis of 3-[(5-Phenyl-1,2,4-oxadiazol-3-yl)methylene]-2-indolinone (CS7145)

3-[(5-Phenyl-1,2,4-oxadiazol-3-yl)methylene]-2-indolinone is synthesized according to Method A.

5.127. Synthesis of 3-[(3-Phenyl-1,2,4-oxadiazol-5-yl)methylene]-2-indolinone (CS7146)

3-[(3-Phenyl-1,2,4-oxadiazol-5-yl)methylene]-2-indolinone is synthesized according to Method A.

5.128. Synthesis of 3-[(3-Phenyl-1,2,5-oxadiazol-4-yl)methylene]-2-indolinone (CS7147)

3-[(3-Phenyl-1,2,5-oxadiazol-4-yl)methylene]-2-indolinone is synthesized according to Method A.

6. EXAMPLES

In Vitro RTK Assays

The following in vitro assays may be used to determine the level of activity and effect of the different compounds of the present invention on one or more of the RTKs. Similar assays can be designed along the same lines for any tyrosine kinase using techniques well known in the art.

6.1. Enzyme Linked Immunosorbent Assay (ELISA)

Enzyme linked immunosorbent assays (ELISA) may be used to detect and measure the presence of tyrosine kinase activity. The ELISA may be conducted according to known protocols which are described in, for example, Voller, et al., 1980, *"Enzyme-Linked Immunosorbent Assay,"* In: *Manual of Clinical Immunology*, 2d ed., edited by Rose and Friedman, pp 359–371 Am. Soc. Of Microbiology, Washington, D.C.

The disclosed protocol may be adapted for determining activity with respect to a specific RTK. For example, the preferred protocols for conducting the ELISA experiments for specific RTKs is provided below. Adaptation of these protocols for determining a compound's activity for other members of the RTK family, as well as non-receptor tyrosine kinases, are within the scope of those in the art.

6.1.1. FLK-1 ELISA

An ELISA assay was conducted to measure the kinase activity of the FLK-1 receptor and more specifically, the inhibition or activation of protein tyrosine kinase activity on the FLK-1 receptor. Specifically, the following assay was conducted to measure kinase activity of the FLK-1 receptor in FLK-1/NIH3T3 cells.

MATERIALS AND METHODS.

Materials. The following reagents and supplies were used:
a. Corning 96-well ELISA plates (Corning Catalog No. 25805–96);
b. Cappel goat anti-rabbit IgG (catalog no. 55641);
c. PBS (Gibco Catalog No. 450–1300EB);
d. TBSW Buffer (50 mM Tris (pH 7.2), 150 mM NaCl and 0.1% Tween-20);
e. Ethanolamine stock (10% ethanolamine (pH 7.0), stored at 4° C.);
f. HNTG buffer (20 mM HEPES buffer (pH 7.5), 150 mM NaCl, 0.2% Triton X-100, and 10% glycerol);
g. EDTA (0.5M (pH 7.0) as a 100X stock);
h. Sodium ortho vanadate (0.5M as a 100X stock);
i. Sodium pyro phosphate (0.2M as a 100X stock);
j. NUNC 96 well V bottom polypropylene plates (Applied Scientific Catalog No. AS–72092);
k. NIH3T3 C7#3 Cells (FLK-1 expressing cells);
l. DMEM with 1X high glucose L Glutamine (catalog No. 11965–050);
m. FBS, Gibco (catalog no. 16000–028);
n. L-glutamine, Gibco (catalog no. 25030–016);
o. VEGF, PeproTech, Inc. (catalog no. 100–20)(kept as 1 $\mu$g/100 $\mu$l stock in Milli-Q dH$_2$O and stored at −20° C.;
p. Affinity purified anti-FLK-1 antiserum, Enzymology Lab, Sugen, Inc.;
q. UB40 monoclonal antibody specific for phosphotyrosine, Enzymology Lab, Sugen, Inc. (see, Fendly, et al., 1990, *Cancer Research* 50:1550–1558);
r. EIA grade Goat anti-mouse IgG-POD (BioRad catalog no. 172–1011);
s. 2,2-azino-bis(3-ethylbenz-thiazoline-6-sulfonic acid (ABTS) solution (100 mM citric acid (anhydrous), 250 mM Na$_2$HPO$_4$ (pH 4.0), 0.5 mg/ml ABTS (Sigma catalog no. A-1888)), solution should be stored in dark at 4° C. until ready for use;

t. $H_2O_2$ (30% solution) (Fisher catalog no. H325);
u. ABTS/$H_2O_2$ (15 ml ABTS solution, 2 μl $H_2O_2$) prepared 5 minutes before use and left at room temperature;
v. 0.2M HCl stock in $H_2O$;
w. dimethylsulfoxide (100%)(Sigma Catalog No. D-8418); and
y. Trypsin-EDTA (Gibco BRL Catalog No. 25200–049).

Protocol. The following protocol was used for conducting the assay:

1. Coat Corning 96-well elisa plates with 1.0 μg per well Cappel Anti-rabbit IgG antibody in 0.1M $Na_2CO_3$ pH 9.6. Bring final volume to 150 μl per well. Coat plates overnight at 4° C. Plates can be kept up to two weeks when stored at 4° C.
2. Grow cells in Growth media(DMEM, supplemental with 2.0 mM L-Glutamine, 10% FBS) in suitable culture dishes until confluent at 37° C., 5% $CO_2$.
3. Harvest cells by trypsinization and seed in Corning 25850 polystyrene 96-well roundbottom cell plates, 25.000 cells/well in 200μl of growth media.
4. Grow cells at least one day at 37° C., 5% $CO_2$.
5. Wash cells with D-PBS 1X.
6. Add 200μl/well of starvation media (DMEM, 2.0 mM l-Glutamine, 0.1% FBS). Incubate overnight at 37° C., 5% $CO_2$.
7. Dilute Compounds/Extracts 1:20 in polypropylene 96 well plates using starvation media. Dilute dimethylsulfoxide 1:20 for use in control wells.
8. Remove starvation media from 96 well cell culture plates and add 162 μl of fresh starvation media to each well.
9. Add 18 μl of 1:20 diluted Compound/Extract dilution (from step 7) to each well plus the 1:20 dimethylsulfoxide dilution to the control wells (+/−VEGF), for a final dilution of 1:200 after cell stimulation. Final dimethylsulfoxide is 0.5%. Incubate the plate at 37° C., 5% $CO_2$ for two hours.
10. Remove unbound antibody from ELISA plates by inverting plate to remove liquid. Wash 3 times with TBSW +0.5% ethanolamine, pH 7.0. Pat the plate on a paper towel to remove excess liquid and bubbles.
11. Block plates with TBSW +0.5% Ethanolamine, pH 7.0, 150 μl per well. Incubate plate thirty minutes while shaking on a microtiter plate shaker.
12. Wash plate 3 times as described in step 10.
13. Add 0.5 μg/well affinity purified anti-FLU-1 polyclonal rabbit antiserum. Bring final volume to 150 μl/well with TBSW +0.5% ethanolamine pH 7.0. Incubate plate for thirty minutes while shaking.
14. Add 180 μl starvation medium to the cells and stimulate cells with 20 μl/well 10.0 mM sodium ortho vanadate and 500 ng/ml VEGF (resulting in a final concentration of 1.0 mM sodium ortho vanadate and 50 ng/ml VEGF per well) for eight minutes at 37° C., 5% $CO_2$. Negative control wells receive only starvation medium.
15. After eight minutes, media should be removed from the cells and washed one time with 200 μl/well PBS.
16. Lyse cells in 150 μl/well HNTG while shaking at room temperature for five minutes. HNTG formulation includes sodium ortho vanadate, sodium pyro phosphate and EDTA.
17. Wash ELISA plate three times as described in step 10.
18. Transfer cell lysates from the cell plate to elisa plate and incubate while shaking for two hours. To transfer cell lysate pipette up and down while scrapping the wells.
19. Wash plate three times as described in step 10.
20. Incubate ELISA plate with 0.02 μg/well UB40 in TBSW +0.05% ethanolamine. Bring final volume to 150 μl/well. Incubate while shaking for 30 minutes.
21. Wash plate three times as described in step 10.
22. Incubate ELISA plate with 1:10,000 diluted EIA grade goat anti-mouse IgG conjugated horseradish peroxidase in TBSW +0.5% ethanolamine, pH 7.0. Bring final volume to 150 μl/well. Incubate while shaking for thirty minutes.
23. Wash plate as described in step 10.
24. Add 100 μl of ABTS/$H_2O_2$ solution to well. Incubate ten minutes while shaking.
25. Add 100 μl of 0.2M HCl for 0.1M HCl final to stop the color development reaction. Shake 1 minute at room temperature. Remove bubbles with slow stream of air and read the ELISA plate in an ELISA plate reader at 410 nm.

6.1.2. HER-2 ELISA

Assay 1: EGF Receptor-HER2 Chimeric Receptor Assay In Whole Cells. HER2 kinase activity in whole EGFR-NIH3T3 cells was measured as described below:

Materials and Reagents. The following materials and reagents were used to conduct the assay:

a. EGF: stock concentration=16.5 ILM; EGF 201, TOYOBO, Co., Ltd. Japan.
b. 05–101 (UBI) (a monoclonal antibody recognizing an EGFR extracellular domain).
c. Anti-phosphotyrosine antibody (anti-Ptyr) (polyclonal) (see, Fendly, et al., supra).
d. Detection antibody: Goat anti-rabbit lgG horse radish peroxidase conjugate, TAGO, Inc., Burlingame, Calif.

| e. TBST buffer: | |
|---|---|
| Tris-HCl, pH 7.2 | 50 mM |
| NaCl | 150 mM |
| Triton X-100 | 0.1 |
| f. HNTG 5X stock: | |
| HEPES | 0.1 M |
| NaCl | 0.75 M |
| Glycerol | 50% |
| Triton X-100 | 1.0% |
| g. ABTS stock: | |
| Citric Acid | 100 mM |
| $Na_2HPO_4$ | 250 mM |
| HCl, conc. | 0.5 pM |
| ABTS* | 0.5 mg/ml |

*(2,2'-azinobis(3-ethylbenzthiazolinesulfonic acid)). Keep solution in dark at 4° C. until use.

h. Stock reagents of:
EDTA 100 mM pH 7.0
$Na_3VO_4$ 0.5M
$Na_4(P_2O_7)$ 0.2M

Procedure. The following protocol was used:

A. Pre-coat ELISA Plate

1. Coat ELISA plates (Corning, 96 well, Cat. #25805–96) with 05-101 antibody at 0.5 g per well in PBS, 100 μl final volume/well, and store overnight at 4° C. Coated plates are good for up to 10 days when stored at 4° C.
2. On day of use, remove coating buffer and replace with 100 μl blocking buffer (5% Carnation Instant Non-Fat Dry Milk in PBS). Incubate the plate, shaking, at room temperature (about 23° C. to 25° C.) for 30 minutes. Just prior to use, remove blocking buffer and wash plate 4 times with TBST buffer.

B. Seeding Cells

1. An NIH3T3 cell line overexpressing a chimeric receptor containing the EGFR extracellular domain and extracellular HER2 kinase domain can be used for this assay.

2. Choose dishes having 80–90% confluence for the experiment. Trypsinize cells and stop reaction by adding 10% fetal bovine serum. Suspend cells in DMEM medium (10% CS DMEM medium) and centrifuge once at 1500 rpm, at room temperature for 5 minutes.

3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 µl per well, in a 96 well microtiter plate. Incubate seeded cells in 5% $CO_2$ at 37° C. for about 40 hours.

C. Assay Procedures

1. Check seeded cells for contamination using an inverted microscope. Dilute drug stock (10 mg/ml in DMSO) 1:10 in DMEM medium, then transfer 5 1 to a TBST well for a final drug dilution of 1:200 and a final DMSO concentration of 1%. Control wells receive DMSO alone. Incubate in 5% $CO_2$ at 37° C. for two hours.

2. Prepare EGF ligand: dilute stock EGF in DMEM so that upon transfer of 10 µl dilute EGF (1:12 dilution), 100 nM final concentration is attained.

3. Prepare fresh HNTG* sufficient for 100 µl per well; and place on ice.

| HNTG* (10 ml): | |
|---|---|
| HNTG stock | 2.0 ml |
| milli-Q $H_2O$ | 7.3 ml |
| EDTA, 100 mM, pH 7.0 | 0.5 ml |
| $Na_3VO_4$, 0.5M | 0.1 ml |
| $Na_4(P_2O_7)$, 0.2M | 0.1 ml |

4. After 120 minutes incubation with drug, add prepared SGF ligand to cells, 10 µl per well, to a final concentration of 100 nM. Control wells receive DMEM alone. Incubate, shaking, at room temperature, for 5 minutes.

5. Remove drug, EGF, and DMEM. Wash cells twice with PBS. Transfer HNTG* to cells, 100 µl per well. Place on ice for 5 minutes. Meanwhile, remove blocking buffer from other ELISA plate and wash with TBST as described above.

6. With a pipette tip securely fitted to a micropipettor, scrape cells from plate and homogenize cell material by repeatedly aspirating and dispensing the HNTG lysis buffer. Transfer lysate to a coated, blocked, and washed ELISA plate. Incubate shaking at room temperature for one hour.

7. Remove lysate and wash 4 times with TBST. Transfer freshly diluted anti-Ptyr antibody to ELISA plate at 100 µl per well. Incubate shaking at room temperature for 30 minutes in the presence of the anti-Ptyr antiserum (1:3000 dilution in TBST).

8. Remove the anti-Ptyr antibody and wash 4 times with TBST. Transfer the freshly diluted TAGO anti-rabbit IgG antibody to the ELISA plate at 100 µl per well. Incubate shaking at room temperature for 30 minutes (anti-rabbit IgG antibody: 1:3000 dilution in TBST).

9. Remove TAGO detection antibody and wash 4 times with TBST. Transfer freshly prepared $ABTS/H_2O_2$ solution to ELISA plate, 100 µl per well. Incubate shaking at room temperature for 20 minutes. ($ABTS/H_2O_2$ solution: 1.0 µl 30% $H_2O_2$ in 10 ml ABTS stock).

10. Stop reaction by adding 50 µl 5N $H_2SO_4$ (optional), and determine O.D. at 410 nm.

11. The maximal phosphotyrosine signal is determined by subtracting the value of the negative controls from the positive controls. The percent inhibition of phosphotyrosine content for extract-containing wells is then calculated, after subtraction of the negative controls.

Assay 2: HER-2-BT474 ELISA. A second assay may be conducted to measure whole cell HER2 activity. Such assay may be conducted as follows:

Materials And Reagents. The following materials and reagents were used:

a. BT-474 (ATCC HBT20), a human breast tumor cell line which expresses high levels of HER2 kinase.

b. Growth media comprising RPMI+10% FBS+GMS-G (Gibco supplement)+glutamine for use in growing BT-474 in an incubator with 5% $CO_2$ at 37° C.

c. A monoclonal anti-HER2 antibody.

| d. D-PBS: | |
|---|---|
| $KH_2PO_4$ | 0.20 g/l 10 (GIBCO, 310-4190AJ) |
| $K_2HPO_4$ | 2.16 g/l |
| KCl | 0.20 g/l |
| NaCl | 8.00 g/l (pH 7.2) | e. Blocking Buffer: TBST plus 5% Milk (Carnation Instant Non-Fat Dry Milk).

| f. TBST buffer: | |
|---|---|
| Tris-HCl | 50 mM |
| NaCl | 150 mM (pH 7.2, HCl 10 N) |
| Triton X-100 | 0.1% | wherein stock solution of TES (10X) is prepared, and Triton X-100 is added to the buffer during dilution.

| g. HNTG buffer (5x): | |
|---|---|
| HEPES | 0.1 M |
| NaCl | 750 mM (pH 7.2 (HCl, 1 N) |
| Glycerol | 50% |
| Triton X-100 | 1.0% |

Stock solution (5×) is prepared and kept in 4° C.

h. EDTA-HCl: 0.5M pH 7.0 (10N HCl) as 500X stock.

i. $Na_3VO_4$: 0.5M as 100X stock is kept at −80° C. as aliquots.

j. $Na_4(P_2O_7)$: 0.2M as 100X stock.

k. Polyclonal antiserum anti-phosphotyrosine.

l. Goat anti-rabbit IgG, horseradish peroxidase (POD) conjugate (detection antibody), Tago (Cat. No. 4520; Lot No. 1802): Tago, Inc., Burlingame, Calif.

| m. ABTS solution: | |
|---|---|
| Citric acid | 100 mM |
| $Na_2HPO_4$ | 250 mM (pH 4.0, 1 N HCl) |
| ABTS | 0.5 mg/ml | wherein ABTS is 2.2'-azinobis(3-ethylbenzthiazoline sulfonic acid). For this assay, the ABTS solution should be kept in the dark at 4° C. The solution should be discarded when it turns green.

n. Hydrogen peroxide: 30% solution is kept in dark and 4° C.

Procedure. All the following steps are at room temperature and aseptically performed, unless stated otherwise. All ELISA plate washing is by rinsing with distilled water three times and once with TBST.

A. Cell Seeding

1. Grow BT474 cells in tissue culture dishes (Corning 25020-100) to 80–90% confluence and collect using Trypsin-EDTA (0.25%, GIBCO).

2. Resuspend the cells in fresh medium and transfer to 96-well tissue culture plates (Corning, 25806-96) at about 25,000–50,000 cells/well (100 μl/well). Incubate the cells in 5% $CO_2$ at 37° C. overnight.

B. ELISA Plate Coating and Blocking

1. Coat the ELISA plate (Corning 25805-96) with anti HER2 antibody at 0.5 μg/well in 150 μl PBS overnight at 4° C., and seal with parafilm. The antibody coated plates can be used up to 2 weeks, when stored at 4° C.

2. On the day of use, remove the coating solution, replace with 200 μl of Blocking Buffer, shake the plate, and then remove the blocking buffer and wash the plate just before adding lysate.

C. Assay Procedures

1. TBST the drugs in serum-free condition. Before adding drugs, the old media is replaced with serum-free RPMI (90 μl/well)

2. Dilute drug stock (in 100% DMSO) 1:10 with RPMI, and transfer 10 μl/well of this solution to the cells to achieve a final drug DMSO concentration at 1%. Incubate the cells in 5% $CO_2$ at 37° C.

| 3. Prepare fresh cell lysis buffer (HNTG*) | |
|---|---|
| 5xHNTG | 2 ml |
| EDTA | 0.2 ml |
| $Na_3VO_4$ | 0.1 ml |
| $Na_4P_2O_7$ | 0.1 ml |
| $H_2O$ | 7.3 ml |

4. After drug preincubation for two hours remove all the solution from the plate, transfer HNTG* (100 μl/well) to the cells, and shake for 10 minutes.

5. Use a 12-channel pipette to scrape the cells from the plate, and homogenize the lysate by repeat aspiration and dispensing. Transfer all the lysate to the ELISA plate and shake for 1 hour.

6. Remove the lysate, wash the plate, add anti-pTyr (1:3,000 with TBST) 100 μl/well, and shake for 30 minutes.

7. Remove anti-pTyr, wash the plate, add goat anti-rabbit IgG conjugated antibody (1:5,000 with TBST) 100 μl/well, and shake for 30 minutes.

8. Remove anti-rabbit IgG antibody, wash the plate, and add fresh $ABTS/H_2O_2$ (1.2 μl $H_2O_2$ to 10 ml ABTS) 100 1/well to the plate to start color development, which usually takes 20 minutes.

9. Measure OD 410 nM, Dynatec MR5000.

6.1.3. PDGF-R ELISA

All cell culture media, glutamine, and fetal bovine serum were purchased from Gibco Life Technologies (Grand Island, N.Y.) unless otherwise specified. All cells were grown in a humid atmosphere of 90–95% air and 5–10% $CO_2$ at 37° C. All cell lines were routinely subcultured twice a week and were negative for mycoplasma as determined by the Mycotect method (Gibco).

For ELISA assays, cells (U1242, obtained from Joseph Schlessinger, NYU) were grown to 80–90% confluency in growth medium (MEM with 10% FBS, NEAA, 1 mM NaPyr and 2 mM GLN) and seeded in 96-well tissue culture plates in 0.5% serum at 25,000 to 30,000 cells per well. After overnight incubation in 0.5% serum-containing medium, cells were changed to serum-free medium and treated with test compound for 2 hr in a 5% $CO_2$, 37° C. incubator. Cells were then stimulated with ligand for 5–10 minutes followed by lysis with HNTG (20 mM Hepes, 150 mM NaCl, 10% glycerol, 5 mM EDTA, 5 mM $Na_3VO_4$, 0.2% Triton X-100, and 2 mM NaPyr). Cell lysates (0.5 mg/well in PBS) were transferred to ELISA plates previously coated with receptor-specific antibody and which had been blocked with 5% milk in TBST (50 mM Tris-HCl pH 7.2, 150 mM NaCl and 0.1% Triton X-100) at room temperature for 30 min. Lysates were incubated with shaking for 1 hour at room temperature. The plates were washed with TBST four times and then incubated with polyclonal anti-phosphotyrosine antibody at room temperature for 30 minutes. Excess anti-phosphotyrosine antibody was removed by rinsing the plate with TBST four times. Goat anti-rabbit IgG antibody was added to the ELISA plate for 30 min at room temperature followed by rinsing with TBST four more times. ABTS (100 mM citric acid, 250 mM $Na_2HPO_4$ and 0.5 mg/mL 2,2'-azino-bis(3-ethylbenzthiazoline-6-sulfonic acid)) plus $H_2O_2$ (1.2 mL 30% $H_2O_2$ to 10 ml ABTS) was added to the ELISA plates to start color development. Absorbance at 410 nm with a reference wavelength of 630 nm was recorded about 15 to 30 min after ABTS addition.

6.1.4. IGF-I ELISA

The following protocol may be used to measure phosphotyrosine level on IGF-I receptor, which indicates IGF-I receptor tyrosine kinase activity.

Materials And Reagents. The following materials and reagents were used:

a. The cell line used in this assay is 3T3/IGF-1R, a cell line which overexpresses IGF-1 receptor.

b. NIH3T3/IGF-1R is grown in an incubator with 5% $CO_2$ at 37° C. The growth media is DMEM+10% FBS (heat inactivated)+2 mM L-glutamine.

c. Anti-IGF-1R antibody named 17-69 is used. Antibodies are purified by the Enzymology Lab, SUGEN, Inc.

| d. D-PBS: | |
|---|---|
| $KH_2PO_4$ | 0.20 g/l |
| $K_2HPO_4$ | 2.16 g/l |
| KCl | 0.20 g/l |
| NaCl | 8.00 g/l (pH 7.2) | e. Blocking Buffer: TBST plus 5% Milk (Carnation Instant Non-Fat Dry Milk).

| f. TBST buffer: | |
|---|---|
| Tris-HCl | 50 mM |
| NaCl | 150 mM (pH 7.2/HCl 10N) |
| Triton X-100 | 0.1% |

Stock solution of TBS (10X) is prepared, and Triton X-100 is added to the buffer during dilution.

| g. HNTG buffer: | |
|---|---|
| HEPES | 20 mM |
| NaCl | 150 mM (pH 7.2/HCl 1N) |
| Glycerol | 10% |
| Triton X-100 | 0.2% |

Stock solution (5X) is prepared and kept at 4° C.

h. EDTA/HCl: 0.5M pH 7.0 (NaOH) as 100X stock.

i. $Na_3VO_4$: 0.5M as 100X stock and aliquots are kept in −80° C.

j. Na$_4$P$_2$O$_7$: 0.2M as 100X stock.
k. Insulin-like growth factor-1 from Promega (Cat# G5111).
l. Polyclonal antiserum anti-phosphotyrosine: rabbit sera generated by Enzymology Lab., SUGEN Inc.
m. Goat anti-rabbit IgG, POD conjugate (detection antibody), Tago (Cat. No. 4520, Lot No. 1802): Tago, Inc., Burlingame, Calif.

| ABTS (2.2'-azinobis(3- n. ethylbenzthiazolinesulfonic acid)) solution: | |
|---|---|
| Citric acid | 100 mM |
| Na$_2$HPO$_4$ | 250 mM (pH 4.0/1 N HCl) |
| ABTS | 0.5 mg/ml |

ABTS solution should be kept in dark and 4° C. The solution should be discarded when it turns green.

o. Hydrogen Peroxide: 30% solution is kept in the dark and at 4° C.

Procedure. All the following steps are conducted at room temperature unless it is specifically indicated. All ELISA plate washings are performed by rinsing the plate with tap water three times, followed by one TBST rinse. Pat plate dry with paper towels.

A. Cell Seeding:
1. The cells, grown in tissue culture dish (Corning 25020-100) to 80–90% confluence, are harvested with Trypsin-EDTA (0.25%, 0.5 ml/D-100, GIBCO).
2. Resuspend the cells in fresh DMEM+10% FBS+2 mM L-Glutamine, and transfer to 96-well tissue culture plate (Corning, 25806-96) at 20,000 cells/well (100 μl/well). Incubate for 1 day then replace medium to serum-free medium (90/μl) and incubate in 5% CO$_2$ and 37° C. overnight.

B. ELISA Plate Coating and Blocking:
1. Coat the ELISA plate (Corning 25805-96) with Anti-IGF-1R Antibody at 0.5 μg/well in 100 μl PBS at least 2 hours.
2. Remove the coating solution, and replace with 100 μl Blocking Buffer, and shake for 30 minutes. Remove the blocking buffer and wash the plate just before adding lysate.

C. Assay Procedures:
1. The drugs are tested in serum-free condition.
2. Dilute drug stock (in 100% DMSO) 1:10 with DMEM in 96-well poly-propylene plate, and transfer 10 μl/well of this solution to the cells to achieve final drug dilution 1:100, and final DMSO concentration of 1.0%. Incubate the cells in 5% CO$_2$ at 37° C. for 2 hours.

| 3. Prepare fresh cell lysis buffer (HNTG*) | |
|---|---|
| HNTG | 2 ml |
| EDTA | 0.1 ml |
| Na$_3$VO$_4$ | 0.1 ml |
| Na$_4$(P$_2$O$_7$) | 0.1 ml |
| H$_2$O | 7.3 ml |

4. After drug incubation for two hours, transfer 10 μl/well of 200 nM IGF-1 Ligand in PBS to the cells (Final Conc.=20 nM), and incubate at 5% CO$_2$ at 37° C. for 10 minutes.
5. Remove media and add 100 μl/well HNTG* and shake for 10 minutes. Look at cells under microscope to see if they are adequately lysed.
6. Use a 12-channel pipette to scrape the cells from the plate, and homogenize the lysate by repeat aspiration and dispense. Transfer all the lysate to the antibody coated ELISA plate, and shake for 1 hour.
7. Remove the lysate, wash the plate, transfer anti-pTyr (1:3,000 with TBST) 100 μl/well, and shake for 30 minutes.
8. Remove anti-pTyr, wash the plate, transfer Tago (1:3, 000 with TBST) 100 μl/well, and shake for 30 minutes.
9. Remove detection antibody, wash the plate, and transfer fresh ABTS/H2O2 (1.2 μl HO$_2$ to 10 ml ABTS) 100 μl/well to the plate to start color development.
10. Measure OD in Dynatec MR5000, which is connected to Ingres.

6.1.5. EGF Receptor ELISA

EGF Receptor kinase activity (EGFR-NIH3T3 assay) in whole cells was measured as described below:

Materials and Reagents. The following materials and reagents were used a. EGF Ligand: stock concentration=16.5 μM; EGF 201, TOYOBO, Co., Ltd. Japan.
b. 05–101 (UBI) (a monoclonal antibody recognizing an EGFR extracellular domain).
c. Anti-phosphotyosine antibody (anti-Ptyr) (polyclonal).
d. Detection antibody: Goat anti-rabbit lgG horse radish peroxidase conjugate, TAGO, Inc., Burlingame, Calif.

| e. TBST buffer: | |
|---|---|
| Tris-HCl, pH 7 | 50 mM |
| NaCl | 150 mM |
| Triton X-100 | 0.1 |
| f. HNTG 5X stock: | |
| HEPES | 0.1 M |
| NaCl | 0.75 M |
| Glycerol | 50 |
| Triton X-100 | 1.0% |
| g. ABTS stock: | |
| Citric Acid | 100 mM |
| Na$_2$HPO$_4$ | 250 mM |
| HCl, conc. | 4.0 pH |
| ABTS* | 0.5 mg/ml |

Keep solution in dark at 4° C. until used.

h. Stock reagents of:
EDTA 100 mM pH 7.0
Na$_3$VO$_4$ 0.5M
Na$_4$ (P$_2$O$_7$) 0.2M Procedure. The following protocol was used:

A. Pre-coat ELISA Plate
1. Coat ELISA plates (Corning, 96 well, Cat. #25805-96) with 05–101 antibody at 0.5 μg per well in PBS, 150 μl final volume/well, and store overnight at 4° C. Coated plates are good for up to 10 days when stored at 4° C.
2. On day of use, remove coating buffer and replace with blocking buffer (5% Carnation Instant NonFat Dry Milk in PBS). Incubate the plate, shaking, at room temperature (about 23° C. to 25° C.) for 30 minutes. Just prior to use, remove blocking buffer and wash plate 4 times with TBST buffer.

B. Seeding Cells
1. NIH 3T3/C7 cell line (Honegger, et al., Cell 51:199–209, 1987) can be use for this assay.
2. Choose dishes having 80–90% confluence for the experiment. Trypsinize cells and stop reaction by adding 10% CS DMEM medium. Suspend cells in DMEM medium (10% CS DMEM medium) and centrifuge once at 1000 rpm, and once at room temperature for 5 minutes.
3. Resuspend cells in seeding medium (DMEM, 0.5% bovine serum), and count the cells using trypan blue. Viability above 90% is acceptable. Seed cells in DMEM medium (0.5% bovine serum) at a density of 10,000 cells per well, 100 μl per well, in a 96 well microtiter plate. Incubate seeded cells in 5% $CO_2$ at 37° C. for about 40 hours.

C. Assay Procedures.

1. Check seeded cells for contamination using an inverted microscope. Dilute drug stock (10 mg/ml in DMSO) 1:10 in DMEM medium, then transfer 5 μl to a test well for a final drug dilution of 1:200 and a final DMSO concentration of 1%. Control wells receive DMSO alone. Incubate in 5% $CO_2$ at 37° C. for one hour.

2. Prepare EGF ligand: dilute stock EGF in DMEM so that upon transfer of 10 μl dilute EGF (1:12 dilution), 25 nM final concentration is attained.

3. Prepare fresh 10 ml HNTG sufficient for 100 μl per well wherein HNTG* comprises: HNTG stock (2.0 ml), milli-Q $H_2O$ (7.3 ml), EDTA, 100 mM, pH 7.0 (0.5 ml), $Na_3VO_4$ 0.5M (0.1 ml) and $Na_4$ ($P_2O_7$), 0.2M (0.1 ml).

4. Place on ice.

5. After two hours incubation with drug, add prepared EGF ligand to cells, 10 μl per well, to yield a final concentration of 25 nM. Control wells receive DMEM alone. Incubate, shaking, at room temperature, for 5 minutes.

6. Remove drug, EGF, and DMEM. Wash cells twice with PBS. Transfer HNTG to cells, 100 μl per well. Place on ice for 5 minutes. Meanwhile, remove blocking buffer from other ELISA plate and wash with TBST as described above.

7. With a pipette tip securely fitted to a micropipettor, scrape cells from plate and homogenize cell material by repeatedly aspirating and dispensing the HNTG* lysis buffer. Transfer lysate to a coated, blocked, and washed ELISA plate. Incubate shaking at room temperature for one hour.

8. Remove lysate and wash 4 times with TBST. Transfer freshly diluted anti-Ptyr antibody to ELISA plate at 100 μl per well. Incubate shaking at room temperature for 30 minutes in the presence of the anti-Ptyr antiserum (1:3000 dilution in TBST).

9. Remove the anti-Ptyr antibody and wash 4 times with TBST. Transfer the freshly diluted TAGO 30 anti-rabbit IgG antibody to the ELISA plate at 100 μl per well. Incubate shaking at room temperature for 30 minutes (anti-rabbit IgG antibody: 1:3000 dilution in TBST).

10. Remove detection antibody and wash 4 times with TBST. Transfer freshly prepared $ABTS/H_2O_2$ solution to ELISA plate, 100 μl per well. Incubate at room temperature for 20 minutes. $ABTS/H_2O_2$ solution: 1.2 μl 30% $H_2O_2$ in 10 ml ABTS stock.

11. Stop reaction by adding 50 μl 5N $H_2SO_4$ (optional), and determine O.D. at 410 nm.

12. The maximal phosphotyrosine signal is determined by subtracting the value of the negative controls from the positive controls. The percent inhibition of phosphotyrosine content for extract-containing wells is then calculated, after subtraction of the negative controls.

6.1.6. Cellular Insulin Receptor ELISA

The following protocol was used to determine whether the compounds of the present invention possessed insulin receptor tyrosine kinase activity.

Materials And Reagents. The following materials and reagents were used to measure phophotyrosine levels on the insulin receptor (indicating insulin receptor tyrosine kinase activity):

1. The preferred cell line was an NIH3T3 cell line (ATCC No. 1658) which overexpresses Insulin Receptor (H25 cells);

2. H25 cells are grown in an incubator with 5% $CO_2$ at 37° C. The growth media is DMEM+10% FBS (heat inactivated)+2 mm L-Glutamine;

3. For ELISA plate coating, the monoclonal anti-IR antibody named BBE is used. Said antibodies was purified by the Enzymology Lab, SUGEN, Inc.;

| 4. D-PBS, comprising: | |
|---|---|
| $KH_2PO_4$ | 0.20 g/l (GIBCO, 310-4190AJ) |
| $K_2HPO_4$ | 2.16 g/l |
| KCl | 0.20 g/l |
| NaCl | 8.00 g/l (pH 7.2); |

5. Blocking Buffer: TBST plus 5% Milk (Carnation Instant Non-Fat Dry Milk);

| 6. TBST buffer, comprising: | |
|---|---|
| Tris-HCl | 50 mM |
| NaCl | 150 mM pH 7.2 (HCl, 1 N) |
| Triton X-100 | 0.1% |

Note: Stock solution of TBS (10X) is prepared, and Triton X-100 is added to the buffer during dilution;

| 7. HNTG buffer, comprising: | |
|---|---|
| HEPES | 20 mM |
| NaCl | 150 mM pH 7.2 (HCl, 1 N) |
| Glycerol | 10% |
| Triton X-100 | 0.2% |

Note: Stock solution (5X) is prepared and kept at 4° C.;

8. EDTA.HCl: 0.5M pH 7.0 (NaOH) as 100X stock;

9. $Na_3VO_4$: 0.5M as 100X stock and aliquots are kept in −80° C.;

10. $Na_4P_2O_7$: 0.2M as 100X stock;

11. Insulin from GIBCO BRL (Cat# 18125039);

12. Polyclonal antiserum Anti-phosphotyrosine: rabbit sera generated by Enzymology Lab., SUGEN Inc.;

13. Detection antibody, preferably goat anti-rabbit IgG, POD conjugate, Tago (Cat. No. 4520: Lot No. 1802): Tago, Inc., Burlingame, Calif.;

| 14. ABTS solution, comprising: | |
|---|---|
| Citric acid | 100 mM |
| $Na_2HPO_4$ | 250 mM pH 4.0 (1 N HCl) |
| ABTS | 0.5 mg/ml | wherein ABTS is 2,2'-azinobis (3-ethylbenathiazoline sulfonic acid) and stored in the dark at 4° C. and discarded when it turns green;

15. Hydrogen Peroxide: 30% solution is kept in the dark and at 40° C.

Protocol. All the following steps are conducted at room temperature unless it is specifically indicated. All ELISA plate washings are performed by rinsing the plate with tap water three times, followed by one TBST rinse. All plates were tapped dry with paper towels prior to use.

A. Cell Seeding:

1. The cells were grown in tissue culture dish (10 cm, Corning 25020-100) to 80–90% confluence and harvested with Trypsin-EDTA (0.25%, 0.5 ml/D-100, GIBCO);

2. Resuspend the cells in fresh DMEM+10% FBS+2 mM L-Glutamine, and transfer to 96-well tissue culture plate (Corning, 25806–96) at 20,000 cells/well (100 μl/well). The cells are then incubated for 1 day. Following such incubation, 0.01% serum medium (90/μl) replaces the old media and the cells incubate in 5% $CO_2$ and 37° C. overnight.

B. ELISA Plate Coating and Blocking:

1. Coat the ELISA plate (Corning 25805–96) with Anti-IR Antibody at 0.5 μg/well in 100 μl PBS at least 2 hours.

2. Remove the coating solution, and replace with 100 μl; blocking Buffer, and shake for 30 minutes. Remove the blocking buffer and wash the plate just before adding lysate.

C. Assay Procedures

1. The drugs are tested in serum-free condition.

2. Dilute drug stock (in 100% DMSO) 1:10 with DMEM in 96-well poly-propylene plate, and transfer 10 μl/well of this solution to the cells to achieve final drug dilution 1:100, and final DMSO concentration of 1.0%. Incubate the cells in 5% $CO_2$ at 37° C. for 2 hours.

| 3. Prepare fresh cells lysis buffer (HNTG*) | |
|---|---|
| HNTG (5x) | 2 ml |
| EDTA | 0.1 ml |
| $Na_3VO_4$ | 0.1 ml |
| $Na_4P_2O_7$ | 0.1 ml |
| $H_2O$ | 7.3 ml |
| HNTG* | 10 ml |

4. After drug incubation for two hours, transfer 10 μl/well of 1 μM insulin in PBS to the cells (Final concentration=100 nM), and incubate at 5% $CO_2$ at 37° C. for 10 minutes.

5. Remove media and add 100 μl/well HNTG* and shake for 10 minutes. Look at cells under microscope to see if they are adequately lysed.

6. Using a 12-channel pipette, scrape the cells from the plate, and homogenize the lysate by repeat aspiration and dispense. Transfer all the lysate to the antibody coated ELISA plate, and shake for 1 hour.

7. Remove the lysate, wash the plate, transfer anti-pTyr (1:3,000 with TBST) 100 μl/well, and shake for 30 minutes.

8. Remove anti-pTyr, wash the plate, transfer Tago (1:3,000 with TBST) 100 μl/well, and shake for 30 minutes.

9. Remove detection antibody, wash the plate, and transfer fresh $ABTS/H_2O_2$ (1.2 μl $H_2O_2$ to 10 ml ABTS) 100 μl/well to the plate to start color development.

10. Measure OD in Dynatec MR5000, which is connected to Ingres. All following steps should follow Ingres instruction.

6.1.7. Experimental Results From ELISA Assays

The experimental results for various compounds according to the invention using the above-described protocols are set forth at Table 1:

TABLE 1

| | ELISA Assay Results | | | | |
|---|---|---|---|---|---|
| COMPOUND | PDGFR IC50 (μM) | FLK-1 IC50 (μM) | EGFR IC50 (μM) | HER2 Kinase IC50 (μM) | IGF-1R IC50 (μM) |
| SU4312 | 19.4 | 0.8 | | | |
| SU4313 | 14.5 | 18.8 | 11 | 16.9 | 8.0 |
| SU4314 | 12 | 0.39 | | | |
| SU4793 | 87.4 | 4.2 | | | |
| SU4794 | | 11.8 | | | |
| SU4798 | | 28.8 | | | |
| SU4799 | | 9 | | | |
| SU4932 | | 2.2 | | | |
| SU4944 | | 8.5 | | | |

TABLE 1-continued

| | ELISA Assay Results | | | | |
|---|---|---|---|---|---|
| COMPOUND | PDGFR IC50 (μM) | FLK-1 IC50 (μM) | EGFR IC50 (μM) | HER2 Kinase IC50 (μM) | IGF-1R IC50 (μM) |
| SU4952 | | 22.6 | | | |
| SU4956 | | | | 22.5 | |
| SU4967 | 7.9 | 11.2 | | | |
| SU4979 | | 20.9 | | | |
| SU4981 | 33.1 | 2.1 | | | |
| SU4982 | | 21.6 | | 39.4 | |
| SU4983 | | 4.1 | | | |
| SU4984 | 5.8 | 1.6 | | 90.2 | |
| SU5204 | | 4 | | 51.5 | |
| SU5205 | | 9.6 | | | |
| SU5208 | | 4.7 | | | |
| SU5214 | | 14.8 | 36.7 | | |
| SU5218 | | 6.4 | | | |
| SU5401 | | 2.9 | | 89.8 | |
| SU5402 | | 0.4 | | | |
| SU5403 | | 1.8 | | | |
| SU5404 | 17 | 0.24 | | | |
| SU5405 | | 23.8 | | | |
| SU5406 | | 0.17 | | | |
| SU5407 | 53.7 | 1.1 | | | |
| SU5408 | | 0.07 | | | |
| SU5416 | 10.8 | 0.11 | | | |
| SU5418 | | 15.4 | | | |
| SU5419 | | 2.3 | | | |
| SU5421 | | 4.6 | | | |
| SU5424 | | 2.4 | | | |
| SU5425 | | 51.4 | | | |
| SU5427 | | 4.5 | | 70.6 | |
| SU5428 | | 8.6 | | | |
| SU5430 | | 73.4 | | | |
| SU5431 | | 41.2 | | | |
| SU5432 | | 22.8 | | | |
| SU5450 | | 4.5 | | 92.6 | |
| SU5451 | | 3.4 | 44 | | |
| SU5453 | 65.5 | 0.14 | | | |
| SU5455 | | 36.2 | | | |
| SU5463 | | 0.18 | | | |
| SU5464 | | 20.3 | | | |
| SU5466 | 86 | 1.6 | | | |
| SU5468 | 55.9 | 2.7 | | | |
| SU5472 | | 8.7 | | | |
| SU5473 | 14.2 | 1.5 | | | |
| SU5474 | | 7.4 | | | |
| SU5477 | | 0.15 | | | |
| SU5480 | | 5.3 | 39.6 | 30.4 | |

6.2. Cell Growth Assays

The following assays may be conducted to measure the effect of the claimed compounds upon cell growth as a result of the compound's interaction with one or more RTKs. Unless otherwise specified, the following assays may be generally applied to measure the activity of a compound against any particular RTK. To the extent that an assay, set forth below, refers to a specific RTK, one skilled in the art would be able to adapt the disclosed protocol for use to measure the activity of a second RTK.

6.2.1. Soft Agar Assay

The soft agar assay may be used to measure the effects of substances on cell growth. Unless otherwise stated the soft agar assays were carried out as follows:

Material And Reagents. The following materials and reagents were used:

a. A water bath set at 39° C. and another water bath at 37° C.

b. 2X assay medium is comprised of 2X Dulbecco's 5Modified Eagle's Medium (DMEM) (Gibco Cat. # CA400-4ANO3) supplemented by the following:

20% Fetal Bovine Serum (FBS) 2 mM sodium pyruvate 4 mM glutamine amine; and 20 mM HEPES Non-essential Amino Acids (1:50 from 100X stock).

c. 1X assay medium made of lX DMEM supplemented with 10% FBS, 1 mM sodium pyruvate, 2 mM glutamine, 10 mM HEPES, non-essential amino acid (1:100 from 100x stock).

d. 1.6% SeaPlaque Agarose in autoclave bottle.

e. Sterile 35 mm Corning plates (FMC Bioproducts Cat. #50102).

f. Sterile 5 ml glass pipets (individually wrapped).

g. Sterile 15 ml and 50 ml conical centrifuge tubes.

h. Pipets and sterile tips.

i. Sterile microcentrifuge tubes.

j. Cells in T75 flasks: SKOV-3 (ATCC HTB77).

k. 0.25% Trypsin solution (Gibco #25200-015).

Procedure. The following procedure was used to conduct the soft agar assay:

A. Procedure for making the base layer

1. Have all the media warmed up in the 37° C. water bath.

2. To make 1X of assay medium+0.8% agar: make a 1:2 (vol:vol) dilution of melted agar (cooled to 39° C.), with 2X assay medium.

3. Keep all media with agar warm in the 39° C. water bath when not in use.

4. Dispense 1 ml of 1X assay medium+0.8% agar into dishes and gently swirl plate to form a uniform base layer. Bubbles should be avoided.

5. Refrigerate base layers to solidify (about 20 minutes). Base layers can be stored overnight in the refrigerator.

B. Procedure for collecting cells

1. Take out one flask per cell line from the incubator; aspirate off medium; wash once with PBS and aspirate off; add 3 ml of trypsin solution.

2. After all cells dissociate from the flask, add 3 ml of 1X assay media to inhibit trypsin activity. Pipet the cells up and down, then transfer the suspension into a 15 ml tube.

3. Determine the concentration of cells using a Coulter counter, and the viability by trypan blue exclusion.

4. Take out the appropriate volume needed to seed 3300 viable cells per plate and dilute it to 1.5 ml with 1X assay medium.

C. Procedure for making the upper 0.4% agarose layer:

1. Add TBST compounds at twice the desired final assay concentration; +1.5 ml of cell suspension in 1X assay medium 10% FBS; +1.5 ml of 1X assay medium+0.8% agarose*: Total=3.0 ml lX media 10% FBS+0.4% agarose with 3300 viable cells/ml, with and without TBST compounds.

*(Made by 1:2 dilution of 2X media with 1.6% agar 30 for the base layer procedure above.)

2. Plate 1 ml of the Assay Mix onto the 1 ml base layer. The duplicates are plated from the 3 ml volume.

3. Incubate the dishes for 2–3 weeks in a 100% humidified, 10% $CO_2$ incubator.

4. Colonies that are 60 microns and larger are scored positive.

6.2.2. Sulforhodamine B (SRB) Growth Assays

The SRB assays may be used to measure the effects of substances on cell growth. The assays are carried out as follows:

Assay 1: 3T3/E/H+TGF-a(T)$_n$ Cell Growth SRB Assay

Materials:
96-well flat bottom sterile plates
96-well round bottom sterile plates sterile 25 ml or 100 ml reservoir pipets, multi-channel pipetman sterile pipet tips sterile 15 ml and 50 ml tubes Reagents:
0.4% SRB in 1% acetic acid 10 mM Tris base 10% TCA 1% acetic acid sterile DMSO (Sigma) compound in DMSO (100 mM or less stock solution)

25% Trypsin-EDTA in Cell Dissociation Solution (Sigma)

Cell line and growth medium:
3T3/E/H+TGF-a(T) (NIH 3T3 clone 7 cells expressing EGF-R/HER2 chimera and TGF-a, tumor-derived autocrine loop cells)

2% calf serum/DMEM+2 mM glutamine

Protocol:

Day 0: Cell Plating:

This part of assay is carried out in a laminar flow hood.

1. Trypsinize cells as usual. Transfer 100 µl of cell suspension to 10 ml of isotone. Count cells with the Coulter Counter.

2. Dilute cells in growth medium to 60,000 cells/ml. Transfer 100 µl of cells to each well in a 96-well flat bottom plate to give 6000 cells/well.

3. Use half of plate (4 rows) for each compound and quadruplicate wells for each compound concentration, a set of 4 wells for medium control and 4 wells for DMSO control.

4. Gently shake plates to allow for uniform attachment of the cells.

5. Incubate the plates at 37° C.in a 10% CO2 incubator.

Day 1: Addition of Compound:

This part of assay is carried out in a laminar flow hood.

1. In 96 well-round bottom plate, add 125 µl of growth medium to columns 3 to 11. This plate is used to titrate out the compound, 4 rows per compound.

2. In a sterile 15 ml tube, make a 2X solution of the highest concentration of compound by adding 8 µl of the compound to a total of 2 ml growth medium for a dilution of 1:250. At this dilution, the concentration of DMSO is 0.4% for a 2X solution or 0.2% for 1X solution on the cells. The starting concentration of the compound is usually 100 µM but this concentration may vary depending upon the solubility of the compound.

3. Transfer the 2X starting compound solution to quadruplicate wells in column 12 of the 96-well round bottom plate. Do 1:2 serial dilutions across the plate from right to left by transferring 125 µl from column 12 to column 11, column 11 to 10 and so on. Transfer 100 µl of compound dilutions onto 100 µl medium on cells in corresponding wells of 96-well flat bottom plate. Total volume per well should be 200 µl.

4. For vehicle control, prepare a 2X solution of DMSO at 0.4% DMSO in growth medium. Transfer 100 µl of the DMSO solution to the appropriate wells of cells. The final concentration of DMSO is 0.2%.

5. For the medium control wells, add 100 µl/well of growth medium to the appropriate wells of cells.

6. Return the plate to the incubator and incubate for 4 days.

Day 5: Development of Assay

This part of assay is carried out on the bench.

1. Aspirate or pour off medium. Add 200 µl cold 10% TCA to each well to fix cells. Incubate plate for at least 60 min. at 4° C.

2. Discard TCA and rinse wells 5 times with water. Dry plates upside down on paper towels.

3. Stain cells with 100 µl/well 0.4% SRB for 10 min.

4. Pour off SRB and rinse wells 5 times with 1% acetic acid. Dry plates completely upside down on paper towels.

5. Solubilize dye with 100 µl/well 10 mM Tris base for 5–10 min. on shaker.

6. Read plates on Dynatech ELISA Plate Reader at 570 nm with reference at 630 nm.

Assay 2: 3T3/EGF-R+TGF-a(T)$_n$Cell Growth SRB Assay

Materials and Reagents same as for Assay 1. Cell line and growth medium: 3T3/EGF-R+TGF-a(T) (NIH 3T3 clone 7 cells expressing EGF-R and TGF-a, tumor-derived autocrine loop cells) 2% calf serum/DMEM+2 mM glutamine Protocol:

Day 0: Cell Plating:

This part of assay is carried out in a laminar flow hood.

1. Trypsinize cells as usual. Transfer 100 µl of cell suspension to 10 ml of isotone. Count cells with the Coulter Counter.

2. Dilute cells in growth medium to 60,000 cells/ml. Transfer 100 µl of cells to each well in a 96-well flat bottom plate to give 6000 cells/well.

3. Use half of plate (4 rows) for each compound and quadruplicate wells for each compound concentration, a set of 4 wells for medium control and 4 wells for DMSO control.

4. Gently shake plates to allow for uniform attachment of the cells.

5. Incubate the plates at 37° C.in a 10% CO2 incubator.

Day 1: Addition of Compound: same as for Assay 1.

Day 5: Development of Assay: same as for Assay 1.

Assay 3: 3T3/PDGF-βR/PDGF-BB(T) Cell Growth SRB Assay

Cell line and growth medium:

3T3/PDGF-βR/PDGF-BB(T) (NIH 3T3 clone 7 cells expressing PDGF β-preceptor and PDGF-BB, from tumors resected from athymic mice) 2% calf serum/ DMEM+2 mM glutamine Protocol:

Day 0: Cell Plating:

This part of assay is carried out in a laminar flow hood.

1. Trypsinize cells as usual. Transfer 200 µl of cell suspension to 10 ml of isotone. Count cells on the Coulter Counter.

2. Dilute cells in growth medium to 60,000 cells/ml. Transfer 100 µl of cells to each well in a 96-well flat bottom plate to give 6000 cells/well.

3. Allow half of plate (4 rows) for each compound and quadruplicate wells for each compound concentration, a set of 4 wells for medium control and 4 wells for DMSO control.

4. Gently shake plates to allow for uniform attachment of the cells to the plate.

5. Incubate the plates at 37° C.in a 10% $CO_2$ incubator.

Day 1: Addition of Compound: same as for Assay 1.

Day 5: Development of Assay: same as for Assay 1.

Assay 4: Human Smooth Muscle Cells (SMC) Growth SRB Assay

Materials and Reagents same as for Assay 1:

Cell line and growth medium:

Human Aortic Smooth Muscle cells (Clonetics) Clonetics's Bullet Kit: Smooth Muscle Basal Medium (SmBM) which is modified MCDB 131 containing fetal bovine serum (5%), hFGF (2 ng/ml), hEGF (0.1 µg/ml), insulin (5.0 ug/ml), gentamicin (50 µg/ml) and amphotericin B (50 ng/ml)

Protocol:

Day 0: Cell plating:

This part of assay is carried out in a laminar flow hood.

1. Trypsinize cells as usual. Transfer 200 µl of cell suspension to 10 ml of isotone. Count cells on the Coulter Counter.

2. Dilute cells in growth medium to 20,000 cells/ml. Transfer 100 µl of cells to each well in a 96-35 well flat bottom plate to give 2000 cells/well.

3. Allow half of plate (4 rows) for each compound and quadruplicate wells for each compound concentration, a set of 4 wells for medium control and 4 wells for DMSO control.

4. Gently shake plates to allow for uniform attachment of the cells to the plate.

5. Incubate the plates at 37° C.in a 10% CO2 incubator.

Day 1: Addition of Compound: same as for Assay 1.

Day 5: Development of Assay: same as for Assay 1.

6.2.3. 3T3 Cell Growth Assay

Assay 1: PDGP-Induced BrdU Incorporation Assay

Materials and Reagents:

(1) PDGF: human PDGF B/B; 1276–956, Boehringer Mannheim, Germany (2) BrdU Labeling Reagent: 10 mM, in PBS (pH7.4), Cat. No. 1 647 229, Boehringer Mannheim, Germany.

(3) FixDenat: fixation solution (ready to use), Cat. No. 1 647 229, Boehringer Mannheim, Germany.

(4) Anti-BrdU-POD: mouse monoclonal antibody conjugated with peroxidase, Cat. No. 1 647 229, Boehringer Mannheim, Germany.

(5) TMB Substrate Solution: tetramethylbenzidine (TMB), ready to use, Cat. No. 1 647 229, Boehringer Mannheim, Germany.

(6) PBS Washing Solution : 1X PBS, pH 7.4, made in house.

(7) Albumin, Bovine (BSA): fraction V powder; A-8551, Sigma Chemical Co., USA.

Protocol (1) 3T3 engineered cell line: 3T3/EGFRc7.

(2)$_n$Cells are seeded at 8000 cells/well in DMEM, 10% CS, 2 mM Gln in a 96 well plate. Cells are incubated overnight at 37° C.in 5% $CO_2$.

(3) After 24 hours, the cells are washed with PBS, and then are serum starved in serum free medium (0%CS DMEM with 0.1% BSA) for 24 hours.

(4) On day 3, ligand (PDGF=3.8 nM, prepared in DMEM with 0.1% BSA) and test compounds are added to the cells simultaneously. The negative control wells receive serum free DMEM with 0.1% BSA only; the positive control cells receive the ligand (PDGF) but no test compound. Test compounds are prepared in serum free DMEM with ligand in a 96 well plate, and serially diluted for 7 test concentrations.

(5) After 20 hours of ligand activation, diluted BrdU labeling reagent (1:100 in DMEM, 0.1% BSA) is added and the cells are incubated with BrdU (final concentration=10 µM) for 1.5 hours.

(6) After incubation with labeling reagent, the medium is removed by decanting and tapping the inverted plate on a paper towel. FixDenat solution is added (50 µl/well) and the plates are incubated at room temperature for 45 minutes on a plate shaker.

(7) The FixDenat solution is thoroughly removed by decanting and tapping the inverted plate on a paper towel. Milk is added (5% dehydrated milk in PBS, 200 µl/well) as a blocking solution and the plate is incubated for 30 minutes at room temperature on a plate shaker.

(8) The blocking solution is removed by decanting and the wells are washed once with PBS. Anti-BrdU-POD solution (1:100 dilution in PBS, 1% BSA) is added (100 µl/well) and the plate is incubated for 90 minutes at room temperature on a plate shaker.

(9) The antibody conjugate is thoroughly removed by decanting and rinsing the wells 5 times with PBS, and the plate is dried by inverting and tapping on a paper towel.

(10) TMB substrate solution is added (100 µl/well) and incubated for 20 minutes at room temperature on a plate shaker until color development is sufficient for photometric detection.

(11) The absorbance of the samples are measured at 410 nm (in "dual wavelength" mode with a filter reading at 490 nm, as a reference wavelength) on a Dynatech ELISA plate reader.

Assay 2: EGF-Induced BrdU Incorporation Assay

Materials and Reagents (1) EGF: mouse EGF, 201; Toyobo,Co., Ltd. Japan
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution : 1X PBS, pH 7.4, made in house.
(7) Albumin, Bovine (BSA): fraction V powder; A-8551, Sigma Chemical Co., USA.

Protocol (1) 3T3 engineered cell line: 3T3/EGFRc7
(2) Cells are seeded at 8000 cells/well in 10% CS, 2 mM Gln in DMEM, in a 96 well plate. Cells are incubated overnight at 37° C.in 5% $CO_2$.
(3) After 24 hours, the cells are washed with PBS, and then are serum starved in serum free medium (0%CS DMEM with 0.1% BSA) for 24 hours.
(4) On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.
5) After 20 hours of ligand activation, diluted BrdU labeling reagent (1:100 in DMEM, 0.1% BSA) is added and the cells are incubated with BrdU (final concentration=10 $\mu$M) for 1.5 hours.
6) After incubation with labeling reagent, the medium is removed by decanting and tapping the inverted plate on a paper towel. FixDenat solution is added (50 $\mu$l/well) and the plates are incubated at room temperature for 45 minutes on a plate shaker.
(7) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.
(8) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.
(9) The antibody conjugate is thoroughly removed by decanting and rinsing the wells 5 times with PBS, and the plate is dried by inverting and tapping on a paper towel.
(10) TMB substrate solution is added (100 $\mu$l/well) and incubated for 20 minutes at room temperature on a plate shaker until color development is sufficient for photometric detection.
(11) The absorbance of the samples are measured at 410 nm (in "dual wavelength" mode with a filter reading at 490 nm, as a reference wavelength) on a Dynatech ELISA plate reader.

Assay 3: EGF-Induced Her2—Driven BrdU Incorporation

Materials and Reagents:

(1) EGF: mouse EGF, 201; Toyobo,Co., Ltd. Japan
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution : 1X PBS, pH 7.4, made in house.
(7) Albumin, Bovine (BSA): fraction V powder; A-8551, Sigma Chemical Co., USA.

Protocol:

(1) 3T3 engineered cell line: 3T3/EGFr/Her2/EGFr (EGFr with a Her2 kinase domain)
(2) Cells are seeded at 8000 cells/well in DMEM, 10% CS, 2 mM Gln in a 96-well plate. Cells are incubated overnight at 370 in 5% $CO_2$.
(3) After 24 hours, the cells are washed with PBS, and then are serum starved in serum free medium (0% CS DMEM with 0.1% BSA) for 24 hours.
(4) On day 3, ligand (EGF=2 nM, prepared in DMEM with 0.1% BSA) and test compounds are added to the cells simultaneously. The negative control wells receive serum free DMEM with 0.1% BSA only; the positive control cells receive the ligand (EGF) but no test compound. Test compounds are prepared in serum free DMEM with ligand in a 96 well plate, and serially diluted for 7 test concentrations.
5) After 20 hours of ligand activation, diluted BrdU labeling reagent (1:100 in DMEM, 0.1% BSA) is added and the cells are incubated with BrdU (final concentration=10 $\mu$M) for 1.5 hours.
(6) After incubation with labeling reagent, the medium is removed by decanting and tapping the inverted plate on a paper towel. FixDenat solution is added (50 $\mu$l/well) and the plates are incubated at room temperature for 45 minutes on a plate shaker.
(7) The FixDenat solution is thoroughly removed by decanting and tapping the inverted plate on a paper towel. Milk is added (5% dehydrated milk in PBS, 200 $\mu$l/well) as a blocking solution and the plate is incubated for 30 minutes at room temperature on a plate shaker.
(8) The blocking solution is removed by decanting and the wells are washed once with PBS. Anti-BrdU-POD solution (1:100 dilution in PBS, 1% BSA) is added (100 $\mu$l/well) and the plate is incubated for 90 minutes at room temperature on a plate shaker.
(9) The antibody conjugate is thoroughly removed by decanting and rinsing the wells 5 times with PBS, and the plate is dried by inverting and tapping on a paper towel.
(10) TMB substrate solution is added (100 $\mu$l/well) and incubated for 20 minutes at room temperature on a plate shaker until color development is sufficient for photometric detection.
(11) The absorbance of the samples are measured at 410 nm (in "dual wavelength" mode with a filter reading at 490 nm, as a reference wavelength) on a Dynatech ELISA plate reader.

Assay 4: IGF1-Induced BrdU Incorporation Assay

Materials and Reagents:

(1) IGF1 Ligand: human, recombinant; G511, Promega Corp, USA.

(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution : 1X PBS, pH 7.4, made in house.
(7) Albumin, Bovine (BSA): fraction V powder; A-8551, Sigma Chemical Co., USA.

Protocol:
(1) 3T3 engineered cell line: 3T3/IGF1r.
(2) Cells are seeded at 8000 cells/well in DMEM, 10% CS, 2 mM Gln in a 96-well plate. Cells are incubated overnight at 37° C.in 5% $CO_2$.
(3) After 24 hours, the cells are washed with PBS, and then are serum starved in serum free medium (0%CS DMEM with 0.1% BSA) for 24 hours.
(4) On day 3, ligand (IGF1=3.3 nM, prepared in DMEM with 0.1% BSA) and test compounds are added to the cells simultaneously. The negative control wells receive serum free DMEM with 0.1% BSA only; the positive control cells receive the ligand (IGF1) but no test compound. Test compounds are prepared in serum free DMEM with ligand in a 96 well plate, and serially diluted for 7 test concentrations.
5) After 16 hours of ligand activation, diluted BrdU labeling reagent (1:100 in DMEM, 0.1% BSA) is added and the cells are incubated with BrdU (final concentration=10 µM) for 1.5 hours.
(6) After incubation with labeling reagent, the medium is removed by decanting and tapping the inverted plate on a paper towel. FixDenat solution is added (50 µl/well) and the plates are incubated at room temperature for 45 minutes on a plate shaker.
(7) The FixDenat solution is thoroughly removed by decanting and tapping the inverted plate on a paper towel. Milk is added (5% dehydrated milk in PBS, 200 µl/well) as a blocking solution and the plate is incubated for 30 minutes at room temperature on a plate shaker.
(8) The blocking solution is removed by decanting and the wells are washed once with PBS. Anti-BrdU-POD solution (1:100 dilution in PBS, 1% BSA) is added (100 µl/well) and the plate is incubated for 90 minutes at room temperature on a plate shaker.
(9) The antibody conjugate is thoroughly removed by decanting and rinsing the wells 5 times with PBS, and the plate is dried by inverting and tapping on a paper towel.
(10) TMB substrate solution is added (100 µl/well) and incubated for 20 minutes at room temperature on a plate shaker until color development is sufficient for photometric detection.
(11) The absorbance of the samples are measured at 410 nm (in "dual wavelength" mode with a filter reading at 490 nm, as a reference wavelength) on a Dynatech ELISA plate reader.

Assay 5: Insulin-Induced BrdU Incorporation Assay
Materials and Reagents:
(1) Insulin: crystalline, bovine, Zinc; 13007, Gibco BRL, USA.
(2) BrdU Labeling Reagent: 10 mM, in PBS (pH7.4), Cat. No. 1 647 229, Boehringer Mannheim, Germany.
(3) FixDenat: fixation solution (ready to use), Cat. No. 1 647 229, Boehringer Mannheim, Germany.
(4) Anti-BrdU-POD: mouse monoclonal antibody conjugated with peroxidase, Cat. No. 1 647 229, Boehringer Mannheim, Germany.
(5) TMB Substrate Solution: tetramethylbenzidine (TMB), ready to use, Cat. No. 1 647 229, Boehringer Mannheim, Germany.
(6) PBS Washing Solution : 1X PBS, pH 7.4, made in house.
(7) Albumin, Bovine (BSA): fraction V powder; A-8551, Sigma Chemical Co., USA.

Protocol:
(1) 3T3 engineered cell line: H25
(2) Cells are seeded at 8000 cells/well in DMEM, 10% CS, 2 mM Gln in a 96 well plate. Cells are incubated overnight at 37° C.in 5% $CO_2$.
(3) After 24 hours, the cells are washed with PBS, and then are serum starved in serum free medium (0% CS DMEM with 0.1% BSA) for 24 hours.
(4) On day 3, ligand (Insulin=10 nM, prepared in DMEM with 0.1% BSA) and test compounds are added to the cells simultaneously. The negative control wells receive serum free DMEM with 0.1% BSA only; the positive control cells receive the ligand (Insulin) but no test compound. Test compounds are prepared in serum free DMEM with ligand in a 96 well plate, and serially diluted for 7 test concentrations.
(5) After 16 hours of ligand activation, diluted BrdU labeling reagent (1:100 in DMEM, 0.1% BSA) is added and the cells are incubated with BrdU (final concentration=10 µM) for 1.5 hours.
(6) After incubation with labeling reagent, the medium is removed by decanting and tapping the inverted plate on a paper towel. FixDenat solution is added (50 µl/well) and the plates are incubated at room temperature for 45 minutes on a plate shaker.
(7) The FixDenat solution is thoroughly removed by decanting and tapping the inverted plate on a paper towel. Milk is added (5% dehydrated milk in PBS, 200 µl/well) as a blocking solution and the plate is incubated for 30 minutes at room temperature on a plate shaker.
(8) The blocking solution is removed by decanting and the wells are washed once with PBS. Anti-BrdU-POD solution (1:100 dilution in PBS, 1% BSA) is added (100 µl/well) and the plate is incubated for 90 minutes at room temperature on a plate shaker.
(9) The antibody conjugate is thoroughly removed by decanting and rinsing the wells 5 times with PBS, and the plate is dried by inverting and tapping on a paper towel.
(10) TMB substrate solution is added (100 µl/well) and incubated for 20 minutes at room temperature on a plate shaker until color development is sufficient for photometric detection.
(11) The absorbance of the samples are measured at 410 nm (in "dual wavelength" mode with a filter reading at 490 nm, as a reference wavelength) on a Dynatech ELISA plate reader.

6.2.4. HUV-EC-C Assay
The following protocol may also be used to measure a compound's activity:
DAY 0
1. Wash and trypsinize HUV-EC-C cells (human umbilical vein endothelial cells, (American Type Culture Collection; catalogue no. 1730 CRL). Wash with ulbecco's phosphate-buffered saline (D-PBS; obtained from Gibco BRL; catalogue no. 14190-029) 2 times at about 1 ml/10 $cm^2$ of tissue culture flask. Trypsinize with 0.05% trypsin-EDTA in non-enzymatic cell dissociation solution (Sigma Chemical Company; catalogue no. C-1544). The 0.05% trypsin was made by diluting 0.25% trypsin/1 mM EDTA (Gibco; catalogue no. 25200-049) in the cell dissociation solution. Trypsinize with about 1 ml/25–30 cm² of tissue culture flask for about 5 minutes at 37° C. After cells have detached from the flask, add an equal volume of assay medium and transfer to a 50 ml sterile centrifuge tube (Fisher Scientific; catalogue no. 05-539-6).

2. Wash the cells with about 35 ml assay medium in the 50 ml sterile centrifuge tube by adding the assay medium, centrifuge for 10 minutes at approximately 200×g, aspirate the supernatant, and resuspend with 35 ml D-PBS. Repeat the wash two more times with D-PBS, resuspend the cells in about 1 ml assay medium/15 cm² of tissue culture flask. Assay medium consists of F12K medium (Gibco BRL; catalogue no. 21127–014)+0.5% heat-inactivated fetal bovine serum. Count the cells with a Coulter Counter®v Coulter Electronics, Inc.) and add assay medium to the cells to obtain a concentration of 0.8–1.0 ×10⁵ cells/ml.

3. Add cells to 96-well flat-bottom plates at 100 µl/well or 0.8–1.0X10⁴ cells/well; incubate ~24 h at 37° C., 5% $CO_2$.

DAY 1

1. Make up two-fold drug titrations in separate 96-well plates, generally 50 µM on down to 0 µM. Use the same assay medium as mentioned in day 0, step 2 above. Titrations are made by adding 90 µl/well of drug at 200 µM (4X the final well concentration) to the top well of a particular plate column. Since the stock drug concentration is usually 20 mM in DMSO, the 200 µM drug concentration contains 2% DMSO.

Therefore, diluent made up to 2% DMSO in assay medium (F12K+0.5% fetal bovine serum) is used as diluent for the drug titrations in order to dilute the drug but keep the DMSO concentration constant. Add this diluent to the remaining wells in the column at 60 µl/well. Take 60 µl from the 120 µl of 200 µM drug dilution in the top well of the column and mix with the 60 µl in the second well of the column. Take 60 µl from this well and mix with the 60 µl in the third well of the column, and so on until two-fold titrations are completed. When the next-to-the-last well is mixed, take 60 µl of the 120 µl in this well and discard it. Leave the last well with 60 µl of DMSO/media diluent as a non-drug-containing control. Make 9 columns of titrated drug, enough for triplicate wells each for 1) VEGF (obtained from Pepro Tech Inc., catalogue no. 100-200, 2) endothelial cell growth factor (ECGF) (also known as acidic fibroblast growth factor, or aFGF) (obtained from Boehringer Mannheim *Biochemica, catalogue no.* 1439 600), and assay media control. ECGF comes as a preparation with sodium heparin.

2. Transfer 50 µl/well of the drug dilutions to the 96-well assay plates containing the 0.8–1.0 ×10⁴ cells/100 µl/well of the HUV-EC-C cells from day 0 and incubate ~2 h at 37° C., 5% $CO_2$.

3. In triplicate, add 50 µl/well of 80 ng/ml VEGF, 20 µg/ml ECGF, or media control to each drug condition. As with the drugs, the growth factor concentrations are 4X the desired final concentration. Use the assay media from day 0 step 2 to make the concentrations of growth factors. Incubate approximately 24 hours at 37° C., 5% $CO_2$. Each well will have 50 µl drug dilution, 50 µl growth factor or media, and 100 ul cells,=200 ul/well total. Thus the 4X concentrations of drugs and growth factors become 1X once everything has been added to the wells.

DAY 2

1. Add ³H-thymidine (Amersham; catalogue no. TRK-686) at 1 µCi/well (10 µl/well of 100 µCi/ml solution made up in RPMI media+10% heat-inactivated fetal bovine serum) and incubate ~24 h at 37° C., 5% $CO_2$. Note: ³H-thymidine is made up in RPMI media because all of the other applications for which we use the ³H-thymidine involve experiments done in RPMI. The media difference at this step is probably not significant. RPMI was obtained from Gibco BRL, catalogue no. 11875-051.

DAY 3

1. Freeze plates overnight at −20° C.

DAY 4

1. Thaw plates and harvest with a 96-well plate harvester (Tomtec Harvester 96⁽ᴿ⁾) onto filter mats (Wallac; catalogue no. 1205–401); read counts on a Wallac Betaplate (T) liquid scintillation counter.

6.2.5. PDGF-R Cellular Assay

The PDGF cellular kinase assay was carried out as follows: cells are lysed in 0.2M Hepes, 0.15M NaCl, 10% V/V glycerol, 0.04% Triton X-100, 5 mM EDTA, 5 mM sodium vanadate and 2 mM Na+pyrophosphate; cell lysates are then added to an ELISA plate coated with an anti-PDGF receptor antibody (Genzyme); ELISA plates are coated at 0.5 µg of antibody/well in 150 µl of PBS for 18 hours at 4° C. prior to the addition of the lysate; the lysate is incubated in the coated plates for 1 hour and then washed four times in TBST (35 mM Tris-HCl pH 7.0, 0.15M NaCl, 0.1% Triton X100); anti-phosphotyrosine antibody (100 µl in PBS) is added and the mixture is incubated for 30 minutes at room temperature; the wells were then washed four times in TBST, a secondary antibody conjugated to POD (TAGO) is added to each well, and the treated well are incubated for 30 minutes at room temperature; the wells are then washed four times in TBST, ABTS/$H_2O_2$ solution is added to each well and the wells are incubated for two minutes; absorbance is then measured at 410 nm.

6.2.6. Experimental Results Of Cell Growth Assay

Results for various compounds obtained from the above-described assays are set forth in the tables that follow:

TABLE 2

Mitogenesis in Endothelial Cells
[3H] Thymidine Incorporation

| | HUV-EC Assay | |
|---|---|---|
| COMPOUND | VEGF (µM) | a-FGF (µM) |
| SU4312 | 1.1 | 153.8 |
| SU4314 | 0.2 | 6.0 |
| SU4793 | 6.6 | 3.4 |
| SU4794 | 4.8 | 35.7 |
| SU4796 | 30.7 | 35.8 |
| SU4798 | 43.2 | |
| SU4799 | 19.9 | |
| SU4932 | 2.5 | 45.2 |
| SU4942 | 1.6 | 4.6 |
| SU4944 | 14.8 | |
| SU4949 | 3.4 | 3.7 |
| SU4952 | 25.6 | 19.3 |
| SU4956 | 8.0 | 13.0 |
| SU4967 | 34.3 | 16.3 |
| SU4972 | 1.0 | 1.4 |
| SU4979 | 4.4 | 4.9 |
| SU4981 | 0.6 | |
| SU4982 | 46.1 | 27.3 |
| SU4984 | 0.8 | 25.8 |
| SU5201 | 2.5 | 2.3 |
| SU5204 | 2.3 | 0.7 |
| SU5205 | 5.1 | 11.8 |
| SU5208 | 2.9 | 130 |
| SU5217 | 9.6 | 10.5 |
| SU5218 | 2.4 | 2.7 |
| SU5401 | 2.2 | |
| SU5402 | <0.8 | 2.0 |

TABLE 2-continued

Mitogenesis in Endothelial Cells
[3H] Thymidine Incorporation

HUV-EC Assay

| COMPOUND | VEGF ($\mu$M) | a-FGF ($\mu$M) |
|---|---|---|
| SU5404 | <0.8 | 31.1 |
| SU5405 | 0.9 | 0.6 |
| SU5406 | <0.8 | |
| SU5407 | 39.8 | 35.5 |
| SU5408 | <0.8 | 22.7 |
| SU5409 | 26.0 | |
| SU5416 | <0.8 | |
| SU5418 | 13.6 | 40 |
| SU5419 | 0.7 | |
| SU5421 | 11.4 | |
| SU5424 | 2.5 | |
| SU5427 | 5.7 | |
| SU5429 | 27.6 | |
| SU5432 | 0.16 | 0.14 |
| SU5438 | 39.8 | 33.0 |
| SU5451 | 1.2 | 30.0 |
| SU5454 | 3.8 | 3.4 |
| SU5455 | 20 | 20 |
| SU5461 | <0.07 | <0.07 |
| SU5462 | 0.5 | 0.8 |
| SU5463 | 0.14 | 7.9 |
| SU5464 | 3.8 | 12.9 |
| SU5466 | 1.3 | 3.2 |
| SU5468 | 0.54 | 8.7 |
| SU5472 | 2.0 | 5.0 |
| SU5473 | 1.2 | 14.1 |
| SU5477 | 0.05 | 37.8 |
| SU5480 | 1.2 | 3.8 |

TABLE 3

Mitogenesis in 3T3/EGFR Cells
BrdU Incorporation

| COMPOUND | PDGFR PDGF Ligand IC50 ($\mu$M) | FGFR FGF Ligand IC50 ($\mu$M) | EGFR EGF Ligand IC50 ($\mu$M) |
|---|---|---|---|
| SU4312 | 75 | | |
| SU4313 | 6 | 5.5 | 5.5 |
| SU4314 | 2.5 | | |
| SU4967 | 9 | 4.9 | 60 |
| SU4981 | 3 | 10 | 20 |
| SU5402 | 50 | 40 | |
| SU5404 | 3 | 25 | |
| SU5406 | 5.2 | | |
| SU5407 | 7.5 | 70 | 100 |
| SU5416 | 2.8 | 70 | |
| SU5451 | 30 | 16 | |
| SU5463 | | | 23 |
| SU5464 | 70 | 60 | 95 |
| SU5465 | 40 | 25 | 50 |
| SU5466 | 18 | 15 | 17 |
| SU5468 | 8 | | |
| SU5469 | 4 | 15 | 28 |
| SU5473 | 4 | 50 | 54 |
| SU5475 | 6.5 | 9 | 48 |

TABLE 4

Cell Growth Assay on Various Cell Lines
SRB Readout

| COMPOUND | 3T3/E/H + TGF-a(T) IC50 ($\mu$M) | 3T3/EGFR + TGF-a(T) IC50 ($\mu$M) | 3T3/PDGFR + PDGF(T) IC50 ($\mu$M) | SMC IC50 ($\mu$M) |
|---|---|---|---|---|
| SU4312 | 36 | | | |
| SU4313 | 32 | 10.7 | | 8.8 |
| SU4314 | 78 | | 10 | |
| SU4984 | | | 22.2 | |

3T3/E/H + TGF-α(T): NIH 3T3 cells expressing EGFR/HER2 chimera and TGF-α, tumor-derived
3T3/EGFR + TGF-α(T): NIH 3T3 cells expressing EGFR and TGF-α, tumor-derived
3T3/PDGFR + PDGF(T): NIH 3T3 cells expressing PDGF-βR and PDGF-ββ, tumor-derived
SMC: human smooth muscle cells from Clonetics

6.3. Measurement Of Cell Toxicity

Therapeutic compounds should be more potent in inhibiting receptor tyrosine kinase activity than in exerting a cytotoxic effect. A measure of the effectiveness and cell toxicity of a compound can be obtained by determining the therapeutic index: $IC_{50}/LD_{50}$. $IC_{50}$, the dose required to achieve 50% inhibition, can be measured using standard techniques such as those described herein. $LD_{50}$, the dosage which results in 50% toxicity, can also be measured by standard techniques (Mossman, 1983, *J. Immunol. Methods*, 65:55–63), by measuring the amount of LDH released (Korzeniewski and Callewaert, 1983, *J. Immunol. Methods* 64:313; Decker and Lohmann-Matthes, 1988, *J. Immunol. Methods* 115:61), or by measuring the lethal dose in animal models. Compounds with a large therapeutic index are preferred. The therapeutic index should be greater than 2, preferably at least 10, more preferably at least 50.

6.3. In Vivo Animal Models

6.3.1. Xenograft Animal Models

The ability of human tumors to grow as xenografts in athymic mice (e.g., Balb/c, nu/nu) provides a useful in vivo model for studying the biological response to therapies for human tumors. Since the first successful xenotransplantation of human tumors into athymic mice, (Rygaard and Povlsen, 1969, *Acta Pathol. Microbial. Scand.* 77:758–760), many different human tumor cell lines (e.g., mammary, lung, genitourinary, gastrointestinal, head and neck, glioblastoma, bone, and malignant melanomas) have been transplanted and successfully grown in nude mice. Human mammary tumor cell lines, including MCF-7, ZR75-l, and MDA-MB-231, have been established as subcutaneous xenografts in nude mice (Warri et al., 1991, *Int. J. Cancer* 49:616–623; Ozzello and Sordat, 1980, *Eur. J. Cancer* 16:553–559; Osborne et al., 1985, *Cancer Res.* 45:584–590; Seibert et al., 1983, *Cancer Res.* 43:2223–2239).

Assay 1: HER2/Xenograft Animal Model

To study the effect of anti-tumor drug candidates on HER2 expressing tumors, the tumor cells should be able to grow in the absence of supplemental estrogen. Many mammary cell lines are dependent on estrogen for in vivo growth in nude mice (Osborne et al., supra), however, exogenous estrogen suppresses HER2 expression in nude mice (Warri et al., supra, Dati et al., 1990, *Oncogene* 5:1001–1006). For example, in the presence of estrogen, MCF-7, ZR-75-1, and T47D cells grow well in vivo, but express very low levels of HER2 (Warri et al., supra, Dati et al., supra).

The following type of xenograft protocol can be used:
1) implant tumor cells (subcutaneously) into the hindflank of five- to six-week-old female Balb/c nu/nu athymic mice;

2) administer the anti-tumor compound;

3) measure tumor growth by measuring tumor volume.

The tumors can also be analyzed for the presence of a receptor, such as HER2, EGF or PDGF, by Western and immunohistochemical analyses. Using techniques known in the art, one skilled in the art can vary the above procedures, for example through the use of different treatment regimes.

Assay 2: FLK-1/Xenograft Model.

The ability of the compounds of the present invention to inhibit ovarian, melanoma, prostate, lung and mammary tumor cell lines established as SC xenografts was examined. These studies were conducted using doses ranging from 1 to 75 mg/kg/day.

Materials And Methods. The tumor cells were implanted subcutaneously into the indicated strains of mice. Treatment was initiated on day 1 post implantation unless otherwise indicated (e.g. treatment of the SCID mouse related to the A375 melanoma cell line began on Day 9). Eight (8) to sixteen (16) mice comprised each test group. Specifically:

Animals. Female athymic mice (BALB/c, nu/nu), BALB/c mice, Wistar rats and Fisher 344 rats were obtained from Simonsen Laboratories (Gilroy, Calif.). Female A/I mice were obtained from Jackson Laboratory (Bar Harbor, Me.). DA rats were obtained from B&K Universal, Inc. (Fremont, Calif.). Athymic R/Nu rats, DBA/2N mice, and BALB/c mice were obtained from Harlan Sprague Dawley (Indianapolis, Ind.). Female C57BL/6 mice were obtained from Taconic (Germantown, N.Y.). All animals were maintained under clean-room conditions in Micro-isolator cages with Alpha-dri bedding. They received sterile rodent chow and water ad libitum.

All procedures were conducted in accordance with the *NIH Guide for the Care and Use Of Laboratory Animals.*

Subcutaneous Xenograft Model. Cell lines were grown in appropriate medium as described (See Section 6). Cells were harvested at or near confluency with 0.05% trypsin-EDTA and pelleted at 450×g for 10 min. Pellets were resuspended in sterile PBS or media (without FBS) to suitable concentration indicated in the Figure legends and the cells were implanted into the hindflank of mice. tumor growth was measured over 3 to 6 weeks using venier calipers and tumor volumes were calculated as a product of length×width× height unless otherwise indicated. P values were calculated using the Students' t-test. Compound in 50–100 $\mu$L excipient (dimethylsulfoxide, BTE, PBTE6C:D5W, or PBTE:D5W) was delivered by IP injection at concentrations indicated in the Figure legends.

Intracerebral Xenograft Model. For the mouse IC model, rat C6 glioma cells were harvested and suspended in sterile PBS at a concentration of $2.5 \times 10^7$ cells/ml and placed on ice. Cells were implanted into BALB/c, nu/nu mice in the following manner: the frontoparietal scalps of mice were shaved with animal clippers if necessary before swabbing with 70% ethanol. animals were anesthetized with isofluorane and the needle as inserted through the skull into the left hemisphere of the brain. Cells were dispensed from Hamilton Gas-tight Syringes using 30 ga ½ inch needles fitted with sleeves that allowed only a 3 mm penetration. A repeater dispenser was used for accurate delivery of 4 $\mu$L of cell suspension. Animals were monitored daily for well-being and were sacrificed when they had a weight loss of about 40% and/or showed neurological symptoms.

For the rat IC model, rats (Wistar, Sprague Dawley, Fisher 344, or athymic R/Nu; approximately 200–400 g (some 3–400 g)) were anesthetized by an IP injection of 100 mg/kg Ketaset (ketamine hydrochloride; Aveco, Fort Dodge, Iowa) and 5 mg/kg Rompun (xylazine, 2% solution; Bayer, Germany). After onset of anesthesia, the scalp was shaved and the animal was oriented in a stereotaxic apparatus (Stoelting, Wood Dale, Ill.). The skin at the incision site was cleaned 3 times with alternating swabs of 70% ethanol and 10% Povidone-Iodine. A median 1.0–1.5 cm incision was made in the scalp using a sterile surgical blade. The skin was detached slightly and pulled to the sides to expose the sutures on the skull surface. A dental drill (Stoelting, Wood Dale, Ill.) was used to make a small (1–2 mm diameter) burrhole in the skull approximately 1 mm anterior and 2 mm lateral to the bregma. The cell suspension was drawn into a 50 $\mu$L Hamilton syringe fitted with a 23 or 25 g a standard bevel needle. The syringe was oriented in the burrhole at the level of the arachnoidea and lowered until the tip of the needle was 3 mm deep into the brain structure, where the cell suspension was slowly injected. After cells were injected, the needle was left in the burrhole for 1–2 minutes to allow for complete delivery of the cells. The skull was cleaned and the skin was closed with 2 to 3 sutures. Animals were observed for recovery from surgery and anesthesia. Throughout the experiment, animals were observed at least twice each day for development of symptoms associated with progression of intracerebral tumor. Animals displaying advanced symptoms (leaning, loss of balance, dehydration, loss of appetite, loss of coordination, cessation of grooming activities, and/or significant weight loss) were humanely sacrificed and the organs and tissues of interest were resected.

Intraperitoneal Model. Cell lines were grown in the appropriate media. Cells were harvested and washed in sterile PBS or medium without FBS, resuspended to a suitable concentration, and injected into the IP cavity of mice of the appropriate strain. Mice were observed daily for the occurrence of ascites formation. Individual animals were sacrificed when they presented with a weight gain of 40%, or when the IP tumor burden began to cause undue stress and pain to the animal.

6.3.2. In Vivo VEGF Pellet Model

In the following example, the Pellet Model was used to test a compound's activity against the FLK-1 receptor and against disorders associated with the formation of blood vessels. In this model, VEGF is packaged into a time-release pellet and implanted subcutaneously on the abdomen of nude mice to induce a 'reddening' response and subsequent swelling around the pellet. Potential FLK-1 inhibitors may then be implanted in methylcellulose near the VEGF pellet to determine whether such inhibitor may be used to inhibit the "reddening" response and subsequent swelling.

Materials And Methods. The following materials were used:

1) VEGF- human recombinant lyophilized product is commercially available and may be obtained from Peprotech, Inc., Princeton Business Park, G2; P.O. box 275, Rocky Hill, N.J. 08553.

2) VEGF packaged into 21 day release pellets were obtained from Innovative Research of America (Innovative Research of America, 3361 Executive Parkway, P.O. Box 2746, Toledo, Ohio 43606), using patented matrix driven delivery system. Pellets were packaged at 0.20, 0.21, or 2.1 mg VEGF/pellet. These doses approximate 10 and 100$\mu$g/day release of VEGF.

3) Methylcellulose

4) Water (sterile)

5) Methanol

6) Appropriate drugs/inhibitors 7) 10 cm culture plates 8) parafilm

The following protocol was then followed to conduct the VEGF pellet model:
1) VEGF, purchased from Peprotech, was sent to Innovative Research for Custom Pellet preparation;
2) Methylcellulose prepared at 1.5% (w/v) in sterile water;
3) Drugs solubilized in methanol (usual concentration range=10 to 20 mg/ml);
4) Place sterile parafilm in sterile 10 cm plates;
5) 150 µl of drug in methanol added to 1.35 ml of 1.5% methylcellulose and mixed/vortexed thoroughly;
6) 25 µl aliquots of homogenate placed on parafilm and dried into discs;
7) Mice (6–10 wk. Balb/C athymic nu/nu, female) were anesthetized via isoflurane inhalation; 8) VEGF pellets and methylcellulose discs were implanted subcutaneously on the abdomen; and
9) Mice were scored at 24 hours and 48 hours for reddening and swelling response.

The specific experimental design used in this example was:
N=4 animals/group
Controls: VEGF pellet+drug placebo VEGF placebo+drug pellet Experimental Results. The compounds of the present invention are expected to demonstrate activity according to this assay.

6.3.3. Mammary Fat Pad Model

Because of the established role played by many of the RTKs, e.g., the HER2 receptor, in breast cancer, the mammary fat pad model is particularly useful for measuring the efficacy of compounds which inhibit such RTKs. By implanting tumor cells directly into the location of interest, in situ models more accurately reflect the biology of tumor development than do subcutaneous models. Human mammary cell lines, including MCF-7, have been grown in the mammary fat pad of athymic mice. Shafie and Grantham, 1981, *Natl. Cancer Instit.* 67:51–56; Gottardis et al., 1988, *J. Steroid Biochem.* 30:311–314. More specifically, the following procedure can be used to measure the inhibitory effect of a compound on the HER2 receptor:
1) Implant, at various concentrations, MDA-MB-231 and MCF-7 cells transfected with HER-2 into the axillary mammary fat pads of female athymic mice;
2) Administer the compound; and
3) Measure the tumor growth at various time points.

The tumors can also be analyzed for the presence of a receptor such as HER2, by Western and immunohistochemical analyses. Using techniques known in the art, one skilled in the art can vary the above procedures, for example through the use of different treatment regimes.

6.3.4. Tumor Invasion Model

The following tumor invasion model has been developed and may be used for the evaluation of therapeutic value and efficacy of the compounds identified to selectively inhibit KDR/FLK-1 receptor.

6.3.4.1. Procedure 8 week old nude mice (female) (Simonsen Inc.) were used as experimental animals. Implantation of tumor cells was performed in a laminar flow hood. For anesthesia, Xylazine/Ketamine Cocktail (100 mg/kg ketamine and 5 mg/kg) are administered intraperitoneally. A midline incision is done to expose the abdominal cavity (approximately 1.5 cm in length) to inject $10^7$ tumor cells in a volume of 100 µl medium. The cells are injected either into the duodenal lobe of the pancreas or under the serosa of the colon. The peritoneum and muscles are closed with a 6-0 silk continuous suture and the skin was closed by using would clips. Animals were observed daily.

6.3.4.2. Analysis

After 2–6 weeks, depending on gross observations of the animals, the mice are sacrificed, and the local tumor metastases, to various organs (lung, liver, brain, stomach, spleen, heart, muscle) are excised and analyzed (measurements of tumor size, grade of invasion, immunochemistry, and in situ hybridization).

6.3.5. RESULTS

Results for various compounds obtained from the above-described in vivo assays are set forth at Table 5, below:

TABLE 5

| | In Vivo Data |
|---|---|
| COMPOUND | EpH4-VEGF % inhibition @ mg/kg |
| SU4312 | 56% @ 75 |
| | 50% @ 75 |
| | 63% @ 50 |
| SU4932 | 42% @ 75 |
| | — |
| | 42% @ 50/50 |
| SU4942 | 46% @ 50 |
| | 47% @ 25 |
| SU5416 | 50% @ 25 |
| | — |
| | 57% @ 37.5/37.5 |
| SU5424 | 45% @ 50 |
| | — |
| | 65% @ 50 |
| SU5427 | 47% @ 50 |
| | — |
| | 65% @ 50 |

The present invention is not to be limited in scope by the exemplified embodiments which are intended as illustrations of single aspects of the invention. Indeed, various modifications of the invention in addition to those described herein will become apparent to those skilled in the art from the foregoing description. Such modifications are intended to fall within the scope of the appended claims.

All references cited herein are hereby incorporated 35 by reference in their entirety.

What is claimed:
1. A compound of the formula

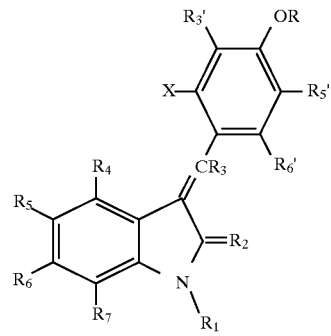

and pharmaceutically acceptable salts thereof, wherein:
$R_1$ is H or alkyl;
$R_2$ is O or S;
$R_3$ is hydrogen,
$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR';

$R_3$' and $R_5$'d $R_6$'] are each independently selected from the group consisting of hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, and CONRR';

$R_6$' is selected from the group consisting of hydrogen, alkyl, alkoxy, aryl, aryloxy, alkaryl, alkaryloxy, halogen, trihalomethyl, S(O)R, SO$_2$NRR', SO$_3$R, SR, NO$_2$, OH, CN, C(O)R, OC(O)R, NHC(O)R, (CH$_2$)$_n$CO$_2$R, and CONRR', n is 0–3;

X is Br, Cl, F or I;

R is H, alkyl or aryl; and

R' is H, alkyl or aryl.

2. The compound of claim 1 wherein:

$R_3$' is selected from the group consisting of methyl, ethyl, n-propyl, iso-propyl, n-butyl, iso-butyl, tert-butyl, halogen, aryl and OR, where R is H, alkyl or aryl; and $R_5$' is selected from the group consisting of hydrogen, methyl, ethyl, n-propyl, iso-propyl, n-butyl, iso-butyl, tert-butyl, halogen, aryl and OR, where R is H, alkyl or aryl.

3. A compound of the formula

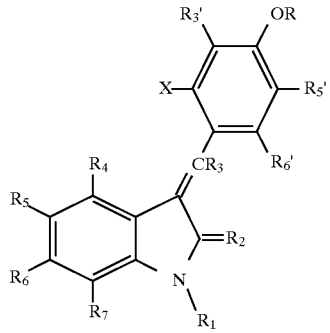

or a pharmaceutically acceptable salt thereof, wherein:

$R_1$ is H or alkyl;

$R_2$ is O or S;

$R_3$ is hydrogen;

$R_4$, $R_5$, $R_6$, and $R_7$ are each independently selected from the group consisting of hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, and CONRR';

n is 0–3;

X is Br, Cl, F or I;

R is H, alkyl or aryl; and

R' is H, alkyl or aryl, with the proviso that if $R_6$' is NRR', then R and R' are not alkyl substituted with N(CH$_3$)$_2$ or amino.

4. The compound 3-(2-chloro-4-hydroxybenzylidenyl)-2-indolinone or a pharmaceutically acceptable salt thereof.

5. The compound 3-(2-chloro-4-methoxybenzylidenyl)-2-indolinone or a pharmaceutically acceptable salt thereof.

6. A pharmaceutical composition comprising a pharmaceutically acceptable carrier or excipient and a compound according to claim 1.

7. The pharmaceutical composition of claim 6, wherein:

$R_3$' is selected from the group consisting of methyl, ethyl, n-propyl, iso-propyl, n-butyl, iso-butyl, tert-butyl, halogen, aryl and OR, where R is H, alkyl or aryl; and $R_5$' is selected from the group consisting of hydrogen, methyl, ethyl, n-propyl, iso-propyl, n-butyl, iso-butyl, tert-butyl, halogen, aryl and OR, where R is H, alkyl or aryl.

8. A pharmaceutical composition comprising a pharmaceutically acceptable carrier or excipient and a compound according to claim 3.

9. A pharmaceutical composition comprising the compound 3-(2-chloro-4-hydroxybenzylidenyl)-2-indolinone or a pharmaceutically acceptable salt thereof, and a pharmaceutically acceptable carrier or excipient.

10. A pharmaceutical composition comprising the compound 3-(2-chloro-4-methoxybenzylidenyl)-2-indolinone or a pharmaceutically acceptable salt thereof, and a pharmaceutically acceptable carrier or excipient.

11. A method for treating diseases related to unregulated tyrosine kinase signal transduction, the method comprising the step of administering to a subject in need thereof a therapeutically effective amount of a compound according to claim 1.

12. The method of claim 4 wherein said disease is selected from the group consisting of cancer, blood vessel proliferative disorders, fibrotic disorders, mesangial cell proliferative disorders and metabolic diseases.

13. The method of claim 12 wherein the blood vessel proliferative disorder is selected from the group consisting of arthritis and restenosis.

14. The method of claim 12 wherein the fibrotic disorder is selected from the group consisting of hepatic cirrhosis and atherosclerosis.

15. The method of claim 12 wherein the mesangial cell proliferative disorder is selected from the group consisting of glomerulonephritis, diabetic nephropathy, malignant nephroscleroris, thrombotic microangiopathy syndromes, transplant rejection and glomerulopathies.

16. The method of claim 12 wherein the metabolic disorder is selected from the group consisting of psoriasis, diabetes mellitus, wound healing, inflammation and neurodegenerative diseases.

17. A method for regulating, modulating or inhibiting tyrosine kinase signal transduction comprising administering to a subject a therapeutically effective amount of a compound according to claim 1.

18. A method for treating diseases related to tyrosine kinase signal transduction, the method comprising the step of administering to a subject in need thereof a therapeutically effective amount of a compound according to claim 3.

19. The method of claim 18 wherein said disease is selected from the group consisting of cancer, blood vessel proliferative disorders, fibrotic disorders, inesangial cell proliferative disorders and metabolic diseases.

20. A method for regulating, modulating or inhibiting tyrosine kinase signal transduction comprising administering to a subject a therapeutically effective amount of a compound according to claim 3.

21. The method of claim 11, wherein said compound is 3-(2-chloro-4-hydroxybenzylidenyl)-2-indolinone.

22. The method of claim 11, wherein said compound is 3-(2-chloro-4-methoxybenzylidenyl)-2-indolinone.

23. The method of claim 17, wherein said compound is 3-(2-chloro-4-hydroxybenzylidenyl)-2-indolinone.

24. The method of claim 17, wherein said compound is 3-(2-chloro-4-methoxybenzylidenyl)-2-indolinone.

* * * * *